United States Patent
Yoshida et al.

(10) Patent No.: US 6,440,431 B1
(45) Date of Patent: Aug. 27, 2002

(54) COSMETIC COMPOSITION

(75) Inventors: Katsunori Yoshida; Toshio Yanaki; Isamu Kaneda, all of Kanagawa (JP)

(73) Assignee: Shiseido Co., Ltd., Tokyo (JP)

( * ) Notice: Subject to any disclaimer, the term of this patent is extended or adjusted under 35 U.S.C. 154(b) by 0 days.

(21) Appl. No.: 09/464,749

(22) Filed: Dec. 16, 1999

(30) Foreign Application Priority Data

Dec. 17, 1998 (JP) .......................................... 10-359390

(51) Int. Cl.⁷ ................................................ A61K 7/00
(52) U.S. Cl. ...................................................... 424/401
(58) Field of Search ......................................... 424/401

(56) References Cited

U.S. PATENT DOCUMENTS

| | | | |
|---|---|---|---|
| 4,079,028 A | | 3/1978 | Emmons et al. |
| 5,281,654 A | | 1/1994 | Eisenhart et al. |
| 5,344,650 A | * | 9/1994 | Otuska et al. ............... 424/401 |

FOREIGN PATENT DOCUMENTS

| | | | |
|---|---|---|---|
| EP | 0761780 A2 | | 3/1997 |
| JP | 0 761 780 A2 | * | 3/1997 |

OTHER PUBLICATIONS

5255040A: Sufactant and Polyether Urethane–Containing Cosmetic Composition, Published Oct. 5, 1993 Japanese Patent Office, Application No. JP1993000018487, Filing Date—Feb. 5, 1993, Applicant—L'Oreal SA.

09071767: Viscosity Modifier, Published Mar. 18, 1997 Japanese Patent Office, Application No. 07229458, Filing Date—Sep. 6, 1995, Applicant—Asahi Denka Kogyo KK.

08283128A: Hairdressing Composition, Published Oct. 29, 1996 by Japanese Patent Office, Application No. 07090534, Filing Date—Apr. 17, 1995, Applicant—KAO Corp.

8325125A: Aerosol Mousse Form Composition Based on Polyurethane and Anionic Polymer, Published Dec. 10, 1996 Japanese Patent Office, Application No. JP1996000116793, Filing Date—May 5, 1996, Applicant—L'Oreal SA.

09071766A: Viscosity Modifier, Published Mar. 18, 1997 Japanese Patent Office, Application No. 07229456, Filing Date—Sep. 6, 1995, Applicant—Asahi Denka Kogyo KK.

10316546A: Hair Dyeing Agent Composition and Thickening The Same, Published Dec. 2, 1998 Japanese Patent Office, Application No. 10123097, Filing Date—May 6, 1998, Applicant—Rohm & Haas Co.

11000549A: Aqueous Composition Containing Mixed Surfactant and Associable Thickener, Published Jan. 6, 1999 Japanese Patent Office, Application No. 10123125, Filing Date—May 6, 1998, Applicant—Rohm & Haas Co.

Franz, Thomas J., "Percutaneous Absorption on the Relevance of In Vitro Data," *The Journal of Investigative Dermatology*, 1975, vol. 64, No. 3, pp. 190–195.

*Encyclopedia of Polymer Science and Engineering*, Second Edition, vol. 17, New York: John Wiley & Sons pp. 772–784 (References under Water–Soluble Polymers).

* cited by examiner

*Primary Examiner*—Jose' G. Dees
*Assistant Examiner*—Konata M. George
(74) *Attorney, Agent, or Firm*—Snider & Associates; Ronald R. Snider

(57) ABSTRACT

In order to provide a cosmetic composition which is excellent in stability of viscosity and usability, the cosmetic composition of the present invention comprises an associative thickener, which is composed of a compound shown in Formula (1), and the cosmetic composition is an oil-in-water emulsion composition, which further comprises a water-soluble polymer:

$$R^1-\{(O-R^2)_k-OCONH-R^3[-NHCOO-(R^4-O)_n-R^5]_h\}_m \quad (1)$$

wherein $R^1$, $R^2$, and $R^4$ each is a hydrocarbon group, which may be the same or different each other; $R^3$ is a hydrocarbon group, which may have urethane bond; $R^5$ is a straight chain, branched chain or secondary hydrocarbon group; m is an integer of 2 or more; h is an integer of 1 or more; and k and n each is an integer within the range of 0 to 1000, respectively.

19 Claims, 5 Drawing Sheets

FIG. 1
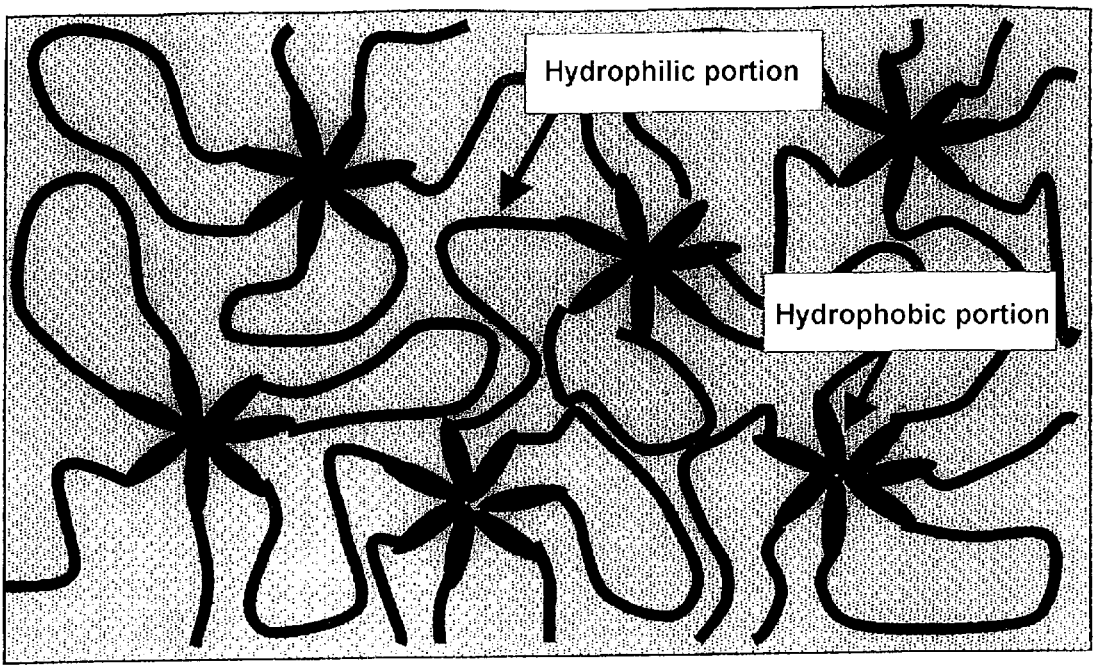
Copolymer(Associative thickener)

FIG. 2

Manufacturing Example A~G

|  | Manufac. Example A | Manufac. Example B | Manufac. Example C | Manufac. Example D | Manufac. Example E | Manufac. Example F | Manufac. Example G |
|---|---|---|---|---|---|---|---|
| $R^1$ | ethylene | ethylene | ethylene | ethylene | dipenta erythritol | penta erythritol | ethylene |
| $R^2$ | ethylene | ethylene | ethylene | ethylene | ethylene | ethylene | ethylene |
| $R^3$ | hexa methylene | hexa methylene | hexa methylene | tetra methylene | tolylene | xylylene | trimethylol propane-hexa methylene diisocyanate |
| $R^4$ | ethylene | ethylene | ethylene | ethylene | propylene | ethylene | ethylene |
| $R^5$ | 2-octyl dodecyl | 2-decyltetra decyl | 2-dodecyl dodecyl | n-octadecyl | 2-hexadecyl octadecyl | 2-hexadecyl octadecyl | 2-ethyldecyl |
| h | 1 | 1 | 1 | 1 | 1 | 1 | 2 |
| m | 2 | 2 | 2 | 2 | 6 | 4 | 2 |
| k | 67 | 67 | 125 | 125 | 35 | 50 | 67 |
| n | 20 | 10 | 20 | 20 | 10 | 20 | 100 |

COSMETIC COMPOSITION

RELATED APPLICATIONS

This application claims the priority of Japanese Patent Application No. 10-359390 filed on Dec. 17, 1998, which is incorporated herein by reference.

FIELD OF THE INVENTION

The present invention relates to a cosmetic composition and, in particular, to an improvement of a thickener to be compounded therein.

BACKGROUND OF THE INVENTION

Various aqueous thickeners are compounded into the cosmetic so as to preserve the form of cosmetic. Examples of organic compound thickeners include natural polymers such as polysaccharides, casein and xanthan gum, and synthetic polymers such as acrylic polymer and carboxyvinyl polymer. Examples of inorganic compound thickeners include various clay minerals such as montmorillonite, and silica and the like. These thickeners have been suitably and selectively used according to its purposes and effects.

In case of using a composition including such thickeners for the cosmetic, stable viscosity i.e., pharmaceutical form can be preserved within various temperature ranges, is required, while the feel in using, i.e., usability and the like are required because the cosmetic is mainly used to the skin as external use.

However, among the cosmetic compositions, which include the conventional thickeners, the composition that sufficiently satisfies stability of viscosity and favorable usability is unknown.

For example, the cosmetic compositions compounding conventional polymer thickeners such as vinyl thickeners and cellulose thickeners, which have been used in the past, are comparatively high in stability and require a small amount of thickener. However, in the case where such composition is used to the skin, sliminess feeling peculiar to polymer is occurred and the composition has unfavorable feeling of use. Also, the cosmetic composition comprising clay mineral has high thixotropic property and refreshing feeling after use, and is favorable in usability. However, such composition is unstable because syneresis occurs easily due to temperature change.

SUMMARY OF THE INVENTION

The present invention is achieved in view of the foregoing prior art, an object of the present invention is to provide a cosmetic composition which is excellent both in stability of viscosity and in usability.

As the result of diligent studies of the present inventors for attaining the above-mentioned object, it has been found that a cosmetic composition, which is excellent both in stability of viscosity and in favorable usability, can be obtained by compounding a specific associative thickener as a main ingredient of thickeners. Further, the present inventors have been found that time stability of viscosity at high temperature and time stability of emulsion in case of an oil-in-water emulsion composition, are improved by using a water-soluble polymer or a polyhydric and monohydric lower alcohols together with the associative thickener. Accordingly the present invention has been accomplished.

Namely, a cosmetic composition of the present invention comprises an associative thickener, which is composed of a compound shown in Formula (1),

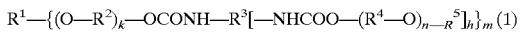

wherein $R^1$, $R^2$, and $R^4$ each is a hydrocarbon group, which may be same or different each other; $R^3$ is a hydrocarbon group, which may have urethane bond; $R^5$ is a straight chain, branched chain or secondary hydrocarbon group; m is an integer of 2 or more; h is an integer of 1 or more; and k and n each is an integer within the range of 0 to 1000, respectively.

Also, in the present invention, it is preferable that the associative thickener is an alkylene group having 2–4 carbon atoms that $R^2$ and/or $R^4$ each may be same or different or phenylethylene group.

It is also preferable that $R^3$ is a residue of polyisocyanate which is shown as $R^3-(NCO)_{h+1}$.

It is also preferable that the polyisocyanate which is shown as $R^3-(NCO)_{h+1}$ is a polyisocyanate having urethane bond, which is obtained by reacting divalent to octavalent polyol with divalent to tetravalent polyisocyanate.

It is also preferable that $R^1$ is a residue of polyol which is shown as $R^1-(OH)_m$.

It is also preferable that $RW^5$ is a straight chain, branched chain or secondary hydrocarbon group having 8–36 carbon atoms.

It is also preferable that the associative thickener is a resultant of one or more of polyetherpolyol that is shown as $R^1-[(O-R^2)_k-OH]_m$, one or more of polyisocyanate that $R^3$ is shown as $R^{-3}(NCO)_{h+1}$, and one or more of polyether monoalcohol shown as $HO-(R^4-O)_n-R^5$.

It is also preferable that the cosmetic composition of the present invention comprises 0.01 to 10 wt % of the associative thickener.

It is also preferable that the cosmetic composition of the present invention further comprises a water-soluble polymer.

It is also preferable that viscosity ratio of water-soluble polymer/associative thickener is 0.01 to 100.

It is also preferable that the cosmetic composition of the present invention further comprises a polyhydric lower alcohol.

It is also preferable that the cosmetic composition of the present invention comprises 0.01 to 10 wt % of the associative thickener and 0.1 to 30 wt % of the polyhydric lower alcohol.

It is also preferable that the cosmetic composition of the present invention further comprises a monohydric lower alcohol.

It is also preferable that the cosmetic composition of the present invention comprises 0.01 to 10 wt % of the associative thickener and 0.1 to 30 wt % of the monohydric lower alcohol.

It is also preferable that the cosmetic composition of the present invention is an oil-in-water emulsion composition.

It is also preferable that the cosmetic composition of the present invention comprises 0.1 to 5 wt % of the associative thickener, 40 wt % or less of an oily ingredient, and 10 times or less of cmc (critical micellar concentration) of an ionic surfactant.

It is also preferable that the cosmetic composition of the present invention comprises 0.1 to 5 wt % of the associative thickener, 40 wt % or less of the oily ingredient, and 10 wt % or less of a nonionic surfactant whose HLB is 12 or less.

It is also preferable that the cosmetic composition of the present invention comprises 0.1 to 5 wt % of the associative thickener, 40 wt % or less of the oily ingredient, and 8 wt % or less of the nonionic surfactant whose ELB is 15 or less.

It is also preferable that the cosmetic composition of the present invention comprises 0.1 to 5 wt % of the associative thickener, 40 wt % or less of the oily ingredient, and 6 wt % or less of the nonionic surfactant whose HLB is 15 or more.

BRIEF DESCRIPTION OF THE DRAWINGS

FIG. 1 is an explanatory drawing of the associative thickener to be compounded into the cosmetic composition in accordance with the present invention.

FIG. 2 shows the associative thickeners to be compounded into the cosmetic compositions of the present invention, which are manufactured by Manufacturing Examples A to G.

BEST MODE FOR CARRYING OUT THE INVENTION

Figure 3:
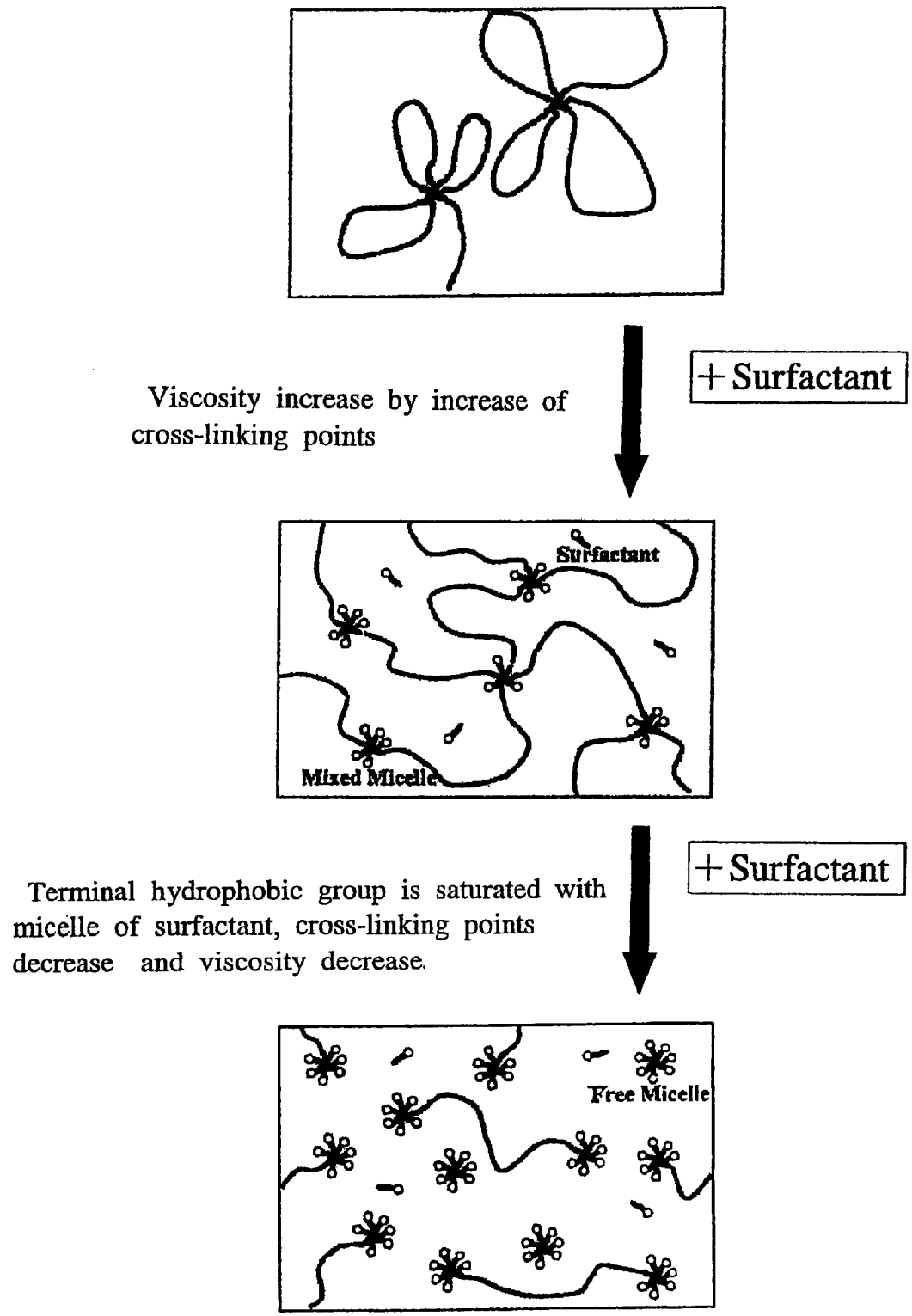
FIG. 3 is an explanatory drawing of thickening mechanism of the associative thickener to be compounded into the cosmetic composition of the present invention, with surfactants.

In the following, the embodiment for carrying out the present invention will be explained in further detail. The present invention has been achieved by the following development process.

A polymer thickening gelling agent is generally used for thickening an aqueous solvent. Some fundamental theories exist in thickening mechanism of the solvent by the polymer. "Chain disentanglement" theory requires that the polymer have extremely high molecular weight that will change considerably large hydrodynamic volume in dissolution condition. Thickening is effected by generating "chain disentanglement" that a solvated long polymer chains are mixed with the other polymer chains. The point of this model are:

(a) interaction of water-soluble thickener polymer chain and latex particle does not exist;
(b) water-soluble thickener polymer chain is drawn or become low viscosity with deforming visco-elastically under shearing condition;
(c) visco-elastic polymer chain recovers and very low fluidity and leveling with respect to aqueous system occur immediately after stopping shearing.

The more established thickener, i.e., usual cellulose derivatives, natural rubber, and synthetic water-soluble polymer of extremely high molecular weight, achieve their thickening mechanism by this "chain disentanglement".

On the other hand, the other theory about thickening polymer in aqueous system is called "associative thickening". This theory is considered as follows. A copolymer which is composed of water-soluble monomer and hydrophobic monomer and which is relatively low molecular weight is associated in aqueous solvent with hydrophobic interaction. The copolymer is cross-linked physically, and accordingly, this action thickens the system with behaving just like one huge molecule (associative thickener is defined in, e.g., Encyclopedia of Polymer Science and Engineering, Second Edition, 17, 772–779). Also, in the case where hydrophobic particle such as latex exists in the system, the same thickening effect is shown by forming physical cross-linking that hydrophobic group of molecule chain adsorbs to the surface of particle. The important aspects of "associative thickening" theory are:

(a) association of molecule hydrophobic group themselves in aqueous solvent or adsorption of polymer hydrophobic group in the surface of hydrophobic particle;

(b) association of molecule themselves or decrease of viscosity by dividing and desorption of adsorption group under shearing or shearing guiding condition, and (c) when shearing force is removed, favorable flow property and leveling property are achieved by increasing viscosity in the controlled velocity by reassociation and adsorption.

The present invention is to provide a cosmetic composition including advanced associative thickener, which is substantiated by this "association thickening" theory.

The associative thickener compounded into the cosmetic composition of the present invention is a copolymer whose skeleton is a hydrophilic group and which has hydrophobic portion in the terminal as shown in FIG. 1. The associative thickener demonstrates thickening action by associating the hydrophobic portions themselves of the copolymer in the water-soluble medium.

The associative thickener copolymer to be compounded into the present invention, to put it concretely, is a hydrophobic denatured polyurethane, which is specified in the following formula:

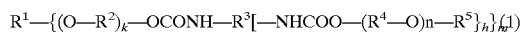

wherein $R^1$, $R^2$, and $R^4$ each is a hydrocarbon group, which may be same or different each other; $R^3$ is a hydrocarbon group, which may have urethane bond; $R^5$ is a straight chain, branched chain or secondary hydrocarbon group; m is an integer more than 2; h is an integer more than 1; and k and n each is an integer within the range of 0 to 1000, respectively.

The hydrophobic denatured polyurethane shown in Formula (1), for example, can be obtained by reacting one or more of polyetherpolyol that is shown as $R^1$—$[(O-R^2)_k-OH]_m$, one or more of polyisocyanate that is shown as $R^3$—$(NCO)_{h+1}$, and one or more of polyether monoalcohol shown as HO—$(R^4-O)_n$—$R^5$.

In here, $R^1$ to $R^5$ in Formula (1) each is determined by the adopted compound, i.e., $R^1$—$[(O-R^2)_k-OH]_m$, $R^3$—$(NCO)_{h+1}$, and HO—$(R^4-O)_n$—$R^5$. Though the ratio of these compounds is not restricted in particular, it is preferable that the ratio of a hydroxyl group originated in polyetherpolyol and polyether monoalcohol to an isocyanate group originated in polyisocyanate is NCO/OH= 0.8:1–1.4:1.

The polyetherpolyol compound shown as $R^1$—$[(O-R^2)_k-OH]_m$, which can be used favorably in order to obtain the associative thickener shown in Formula 1, is manufactured with addition polymerization of alkylene oxide such as ethylene oxide, propylene oxide, butylene oxide, epichlorohydrin, styrene oxide, and the like with m-valent polyol.

As the polyol, divalent to octavalent polyols are preferable, and the examples include: divalent alcohols such as ethylene glycol, propylene glycol, butylene glycol, hexamethylene glycol, and neopentyl glycol; trivalent alcohols such as glycerin, trioxyisobutane, 1,2,3-butanetriol, 1,2,3-pentatriol, 2-methyl-1,2,3-propanetriol, 2-metyl-2,3,4-butanetriol, 2-ethyl-1,2,3-butanetriol, 2,3,4-pentanetriol, 2,3,4-hexanetriol, 4-propyl-3,4,5-heptanetriol, 2,4-dimethyl-2,3,4-pentanetriol, pentamethylglycerine, pentaglycerine, 1,2,4-butanetriol, 1,2,4pentanetriol, trimethylolethane, and trimethylolpropane; tetravalent alcohols such as pentaerythritol, 1,2,3,4-pentanetetrol, 2,3,4,5-hexanetetrol, 1,2,4,5-pentanetetrol and 1,3,4,5-hexanetetrol; pentavalent alcohols such as adonitol, arabitol and xylitol; hexavalent alcohols such as sorbitol, mannitol and iditol; and octavalent alcohols such as sucrose.

Also, alkylene oxide or styrene oxide having 2–4 carbon atoms is preferable in order to demonstrate excellent effect and easiness for acquisition in consideration that $R^2$ is determined according to the alkylene oxide, styrene oxide and the like to be added.

The alkylene oxide, styrene oxide and the like to be added each may be homopolymerization, or random polymerization or block polymerization more than two. The addition method may be a conventional method. Also, polymerization degree k is 0–1000, and preferably is 1–500, and more preferably is 10–200. The associative thickener, which is suitable for the present object, can be obtained in the case where the percentage of the ethylene group in $R^2$ is 50–100 wt % with respect to the whole amount of $R^2$.

Also, the molecular weight of $R^1$—$[(O—R^2)_k—OH]_m$ is preferably 500–100000, and more preferably is 1000–50000.

The polyisocyanate shown as $R^3$—$(NCO)_{h+1}$, which can be used favorably in order to obtain the hydrophobic denatured polyether urethane shown in Formula 1, is not restricted in particular as long as the polyisocyanate has two or more isocyanate group in the molecule. Examples of the polyisocyanate include aliphatic diisocyanates, aromatic diisocyanates, alicyclic diisocyanates, biphenyl diisocyanates, diisocyanates of phenylmethane, triisocyanates, tetraisocyanates, and the like.

Examples of aliphatic diisocyanates include methylene diisocyanate, dimethylene diisocyanate, trimethylene diisocyanate, tetramethylene diisocyanate, pentamethylene diisocyanate, hexamethylene diisocyanate, dipropylether diisocyanate, 2,2-dimethylpentane diisocyanate, 3-methoxyhexane diisocyanate, octamethylene diisocyanate, 2,2,4-trimethylpentane diisocyanate, nonamethylene diisocyanate, decamethylene diisocyanate, 3-butoxyhexane diisocyanate, 1,4-butyleneglycol dipropylether diisocyanate, thiodihexyl diisocyanate, metaxylylene diisocyanate, paraxylylene diisocyanate, tetramethylxylylene diisocyanate and the like.

Examples of aromatic diisocyanates include metaphenylene diisocyanate, paraphenylene diisocyanate, 2,4-tolylene diisocyanate, 2,6-tolylene diisocyanate, dimethylbenzene isocyanate, ethylbenzene diisocyanate, isopropylbenzene diisocyanate, tolidine diisocyanate, 1,4-naphthalene diisocyanate, 1,5-naphthalene diisocyanate, 2,6-naphthalene diisocyanate, 2,7-naphthalene diisocyanate and the like.

Examples of alicyclic diisocyanates include hydrogenated xylylene diisocyanate, isophorone diisocyanate and the like.

Examples of biphenyl diisocyanates include biphenyl diisocyanate, 3,3'-dimethylbiphenyl diisocyanate, 3,3'-dimethoxybiphenyl diisocyanate and the like.

Examples of diisocyanates of phenylmethane include diphenylmethane-4,4'-diisocyanate, 2,2'-dimethyldiphenylmethane4,4'-diisocyanate, diphenyldimethylmethane-4,4'-diisocyanate, 2,5,2',5'-tetramethyldiphenyl-methane-4,4'-diisocyanate, cyclohexylbis (4-isocyonthophenyl) methane, 3,3'-dimethoxy-diphenylmethane-4,4'-diisocyanate, 4,4'-dimethoxydiphenylethane-3,3'-diisocyanate, 4,4'-diethoxydiphenylmethane-3,3'-diisocyanate, 2,2'-dimethyl-5,5'-dimethoxydiphenylmethane-4,4'-diisocyanate, 3,3'-dichlorodiphenyldimethylmethane-4,4'-diisocyanate, benzophenone-3,3'-diisocyanate and the like.

Examples of triisocyanates include 1-methylbenzene-2,4,6-triisocyanate, 1,3,5-trimethylbenzene-2,4,6-triisocyanate, 1,3,7-naphthalenetriisocyanate, biphenyl-2,4,4'-triisocyanate, diphenylmethane-2,4,4'-triisocyanate, 3-methyldiphenylmethane-4,6,4'-triisocyanate, triphenylmethane-4,4',4"-triisocyanate, 1,6,11-undecane triisocyanate, 1,8-diisocyanate4-isocyanatemethyloctane, 1,3,6-hexamethylene triisocyanate, bicycloheptane triisocyanate, tris (isocyanatephenyl) thiophosphate, and the like.

The polyisocyanate of the present invention may be a dimer or trimer (isocyanurate bond) of these polyisocyanate compounds, and also may be used as a biuret by reacting with amine.

Further, the polyisocyanate having urethane bond, that the polyol reacted with these polyisocyanate compounds, may be used. As the polyol, divalent to octavalent polyols, which were mentioned hereinbefore are preferable. Also, the polyisocyanate having urethane bond is preferable in the case where the polyisocyanates more than trivalent polyisocyanate is used as $R^3$—$(NCO)_{h+1}$.

The polyether monoalcohol shown as HO—$(R^4—O)_n$—$R^5$, which can be used favorably in order to obtain the hydrophobic modified polyether urethane shown in Formula 1, is not restricted in particular as long as the polyether monoalcohol is a straight, branched or secondary monohydric alcohol polyether. Such compounds can be obtained by addition polymerization of alkylene oxide such as ethylene oxide, propylene oxide, butylene oxide, epichlorohydrin, styrene oxide, and the like with the straight, branched or secondary monohydric alcohol.

The straight chain alcohol mentioned here can be shown in the following Formula (2).

$$R^6—OH \qquad (2)$$

Also, the branched chain alcohol mentioned here can be shown in the following Formula (3).

$$R^7—\underset{\underset{R^8}{|}}{CH}—R^9—OH \qquad (3)$$

Also, the secondary alcohol mentioned here can be shown in the following Formula

$$R^{10}—\underset{\underset{R^{11}}{|}}{CH}—OH \qquad (4)$$

Accordingly, $R^5$ is a group excluding a hydroxyl group in the above-mentioned Formulae (2) to (4).

In the above-mentioned Formulae (2) to (4), $R^6$, $R^7$, $R^8$, $R^{10}$, and $R^{11}$ each is a hydrocarbon group or fluorocarbon group, and examples of them include an alkyl group, an alkenyl group, an aryl group, and a cycloalkyl and cycloalkenyl group.

Examples of the alkyl group include a methyl, ethyl, propyl, isopropyl, butyl, isobutyl, tertiary butyl, pentyl, isopentyl, neopentyl, tertiary pentyl, hexyl, heptyl, octyl, 2-ethylhexyl, nonyl, decyl, undecyl, dodecyl, tridecyl, isotridecyl, myristyl, palmityl, stearyl, isostearyl, icosyl, docosyl, tetracosyl, thoriacontyl, 2-octyldodecyl, 2-dodecylhexadecyl, 2-tetradecyl-octadecyl and monomethyl branched isostearyl groups.

Examples of the alkenyl group include a vinyl, allyl, propenyl, isopropenyl, butenyl, pentenyl, isopentenyl, hexenyl, heptenyl, octenyl, nonenyl, decenyl, undecenyl, dodecenyl, tetradecenyl and oleyl group.

Examples of the alkyl aryl group include a phenyl, toluyl, xylyl, cumenyl, mesityl, benzyl, phenethyl, styryl, cinnamyl, benzhydryl, trityl, ethylphenyl, propylphenyl, butylphenyl, pentylphenyl, hexylphenyl, heptylphenyl, octylphenyl, nonylphenyl, α-naphthyl, and β-naphthyl group.

Examples of the cycloalkyl and cycloalkenyl group include a cyclopentyl, cyclohexyl, cycloheptyl, methylcyclopentyl, methylcyclohexyl, methylcycloheptyl, cyclopentenyl, cyclohexenyl, cycloheptenyl, methylcyclopentenyl, methylcyclohexenyl, and methylcycloheptenyl group.

In the above-mentioned Formula (3), $R^9$ is a hydrocarbon group or fluorocarbon group, and examples of them include an alkylene group, an alkenylene group, an alkyl arylene group, and a cycloalkylene and cycloalkenylene group.

Also, $R^5$ is a hydrocarbon group or fluorocarbon group, and preferably is an alkyl group. The total carbon atoms is preferably 8–36, and more preferably is 12–24.

The alkylene oxide, styrene oxide and the like to be added each may be homopolymerization, or random polymerization or block polymerization more than two. The addition method may be a conventional method. Also, polymerization degree n is 0–1000, and preferably is 1–200, and more preferably, is 10–200. The associative thickener, which is suitable for the present object can be obtained in the case where the percentage of the ethylene group in $R^4$ is 50–100 wt % and more preferably is 65–100 wt % with respect to the whole amount of $R^4$.

As the manufacturing method of the compound shown in Formula (1), for example, the compound can be obtained by reacting polyether and isocyanate for 1–3 hours at 80–90° C. as like a conventional reaction.

Also, a by-product, which is not the compound having structure of Formula (1) may be produced in the case where polyether polyol (a) shown as $R^1$—[(O—$R^2$)$_k$—OH]$_m$, polyisocyanate (b) shown as $R^3$—(NCO)$_{h+1}$, and polyether monoalcohol (c) shown as HO—($R^4$—O)$_n$—$R^5$ reacted. For example, when diisocyanate is used, the by-products such as c—b—c and c—b—(a—b)$_x$—a—b—c compounds may be produced together with the main product of c—b—a—b—c compound, which is shown in Formula (1). In this case, such by-product can be used in the condition of the mixture, which includes the Formula (1) type compound without separating the Formula (1) compound in particular.

Amount of Associative Thickener

It is preferable to compound 0.01 to 10 wt % of said associative thickener into the cosmetic composition of the present invention. The effect of addition is not observed in the case where the amount of said associative thickener is less than 0.01 wt %. On the other hand, in the case where the amount of said associative thickener is more than 10 wt %, viscosity at heating and dissolution time becomes too much high and it is something wrong to handle at manufacturing time. Accordingly, it is not preferable because efficiency is deteriorated and stickiness is occurred.

Water-Soluble Polymer

The associative thickener that is compounded into the cosmetic composition of the present invention is excellent in usability and stability of viscosity against external factors such as temperature. However, the associative thickener sometimes may be inferior in time stability of viscosity at high temperature. Also, in the case where the cosmetic composition, in particular, is an oil-in-water emulsion composition, long-term emulsion stability may be inferior because the viscosity under low-shearing condition is low. Such problems can be resolved by using water-soluble polymers, polyhydric lower alcohols, or monohydric lower alcohol together with the associative thickener.

In the cosmetic composition of the present invention, time stability of viscosity at high temperature can be improved in the case where the water-soluble polymer is used together with the associative thickener. Also, in the case where the cosmetic composition, in particular, is an oil-in-water emulsion composition, time stability of emulsion can be improved because the viscosity under low-shearing condition is increased by using water-soluble polymer together with the associative thickener. The thickeners, which are usually compounded into cosmetic, can be used as the water-soluble polymer used in the present invention. Examples of the water-soluble polymer include: natural polymers such as guar gum, locust bean gum, quince seed, carageenan, galactan, Arabian gum, tragacanth gum, pectin, mannan, starch, xanthane gum, dextran, succinoglucan, curdlan, hyaluronic acid, gelatin, albumin and collagen; synthetic polymers such as polyvinyl alcohol, polyvinyl pyrrolidone, carboxyvinyl polymer, sodium polyacrylate, polyethylene oxide having tens of thousands of molecular weight (polyethylene oxide having low molecular weight is unsuitable for the water-soluble polymer of the thickener in the present invention), and block copolymer of ethylene oxide/propylene oxide; and semisynthetic polymers such as methylcellulose, ethylcellulose, hydroxyethyl cellulose, hydroxypropyl cellulose, carboxymethyl cellulose, methylhydroxypropyl cellulose, soluble starch, carboxymethyl starch, methyl starch, propyleneglycol alginate and alginate.

The viscosity ratio (water-soluble polymer/associative thickener) of thickener used in the present invention is preferably 0.01 to 100. The viscosity ratio mentioned in the present invention is defined as follows. Water solutions having equal weight with the sample of cosmetic composition are prepared with respect to equal weight of the associative thickener and water-soluble polymer in the sample of cosmetic composition. Viscosity of each solution was measured separately and viscosity ratio of water-soluble polymer/associative thickener.

Namely, in the case where the cosmetic composition is 1 wt % of the associative thickener +0.1 wt % of the water-soluble polymer, viscosity ratio becomes (viscosity of 0.1 wt % of water-soluble polymer solution/viscosity of 1 wt % of associative thickener solution).

Also, the viscosity of solutions was measured by the Brookfield viscometer at 25° C.

In the case where viscosity ratio is less than 0.01, time stability may not be obtained, and time stability of emulsion may be inferior in the oil-in-water emulsion composition because improvement property of viscosity may not be obtained under low-shearing condition. On the other band, in the case where viscosity ratio is more than 100, it is unfavorable because influence of the water-soluble polymer becomes strong and stability of viscosity is deteriorated due to external functions such as salt level or temperature.

Polyhydric Lower Alcohol

In the present invention, time stability of viscosity at high temperature of the associative thickener, and time stability of emulsion particular in the oil-in-water emulsion composition can be improved by compounding a polyhydric lower alcohol. The usual polyhydric lower alcohol compounded into cosmetic can be used as the polyhydric lower alcohol. Examples of the polyhydric lower alcohol include glycerin, propylene glycol, 1,3-butylene glycol, ethylene glycol, and sorbitol. An amount of said polyhydric lower alcohol is preferably 0.1–30 wt %. In the case where the amount of the polyhydric lower alcohol is less than 0.1 wt %, improvement of time stability of viscosity at high temperature may not be obtained, and time stability of emulsion may be inferior in the oil-in-water emulsion composition. On the other hand, in the case where the amount of the polyhydric lower alcohol is more than 30 wt %, it is unfavorable because thickening effect of associative thickener may be decreased and the feeling of use may be spoiled, e.g. stickiness feeling may occur.

Monohydric Lower Alcohol

By using a monohydric lower alcohol, time stability of viscosity at high temperature and time stability of emulsion in the oil-in-water emulsion can be improved. The usual alcohol compounded into cosmetic can be used as the monohydric lower alcohol. Examples of the monohydric lower alcohol include ethanol, propanol and isopropanol. Though monohydric lower alcohols often deteriorate viscosity in the usual thickener, time stability of viscosity at high temperature and time stability of emulsion in the oil-in-water emulsion composition can be improved in the present invention. It is preferable that an amount of said monohydric lower alcohol is 0.1–30 wt %. In the case where the amount of the monohydric lower alcohol is less than 0.1 wt %, improvement of time stability of viscosity at high temperature may not be improved, and time stability of emulsion may not be obtained in the oil-in-water emulsion composition. On the other hand, in the case where the amount of the monohydric lower alcohol is more than 30 wt %, it is unfavorable because viscosity of the associative thickener may be deteriorated.

Oil-in-Water Emulsion Composition

It is possible to use favorably approximately 40 wt % of an oily ingredient which is usually used for cosmetic in the case where the cosmetic composition of the present invention is used as an oil-in-water emulsion composition. Also, viscosity of the associative thickener can be increased by existence of proper amount of surfactant in the present invention. An ionic surfactant such as anionic surfactants, cationic surfactants, and amphoteric surfactants, and a nonionic surfactant, which are generally used in cosmetic can be used as the surfactant of the present invention. As an amount of the surfactant, in the system where 0.1–5 wt % of the associative thickener of the present invention and 40 wt % or less of the oily ingredient are comprised, it is preferable that the amount of the surfactant is ten times or less of cmc (critical micellar concentration), 10 wt % or less, 8 wt % or less and more preferably 4 wt % or less, and 6 wt % or less and more preferably 2 wt % or less in the case where the surfactant is the ionic surfactant, the nonionic surfactant whose HLB is 12 or less, the nonionic surfactant whose HLB is 15 or less, and the nonionic surfactant whose HLB is 15 or more, respectively. The excellent improvement effect of viscosity may not be obtained in the case where the amount is not within the range mentioned hereinbefore.

Humectant

Synergetic effect with the associative thickener in improvement of moisture retention function can be obtained by compounding a humectant into the cosmetic composition of the present invention. In addition to the above-mentioned polyhydric alcohols, the humectant which is generally used for cosmetic can be used as the humectant of the present invention.

Pharmaceutia

Synergetic effect with the associative thickener in improvement of percutaneous absorption promoting effect of pharmaceutical can be obtained by compounding a pharmaceutical into the cosmetic composition of the present invention. Examples of the pharmaceutical that can demonstrate percutaneous absorption promoting effect include α-hydroxy acid such as lactic acid. Relaxation effect against irritation such as smart can be obtained in the case where the pharmaceutical such as α-hydroxy acid, which is possible to involve irritation is compounded into the cosmetic composition of the present invention.

Other Ingredients

As for the other ingredients compounded into the cosmetic composition of the present invention, perfumes, ultraviolet absorbers, resins and the like, which are generally used in cosmetic are listed. These ingredients can be compounded within the range that effect of the cosmetic composition of the present invention is not spoiled.

In the following, the present invention will be explained in further detail according to Manufacturing Examples and Working Examples. The present invention, not tot mention, is not restricted to these Working Examples. Also, the amount will be shown as wt % without otherwise stated.

First, Manufacturing Examples of Associative thickener A–G, which are compounded into the cosmetic composition of the present invention will be described.

<Manufacturing Example A>

To a container that is a four necks flask of 1000 mL that a thermometer, nitrogen introducing pipe, and a disperser are attached, were added 480 parts of polyethylene glycol (PEG) 6000 (molecular weight approximately 6000) (equal to $R—^1[(O—R^2)_k—OH]_m$) and 198 parts of ethylene oxide (EO) 20 mols adduct of the branched alcohol shown in the following Formula (5) (equal to $HO—(R^4—O)_n—R^5$). The mixture was dehydrated for 3 hours at 90–100° C. under reduced pressure and moisture content of the system was 0.03 wt %. Then, it was cooled down to 80° C. 29.6 parts of hexamethylene diisocyanate (HMDI) (equal to $R^3—(NCO)_{h+1}$) was added thereto and it was reacted for 2 hours at 80–90° C. under nitrogen gas atmosphere. After confirming that isocyanate is 0% and a resultant, which is light-yellow solid in normal temperature was obtained. This solid is defined as Associative thickener A.

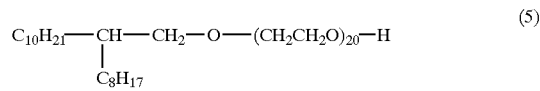

(5)

<Manufacturing Example B>

A light-yellow solid resultant was obtained from 522 parts of PEG 6000, 145 parts of EO 10 mols adduct of the branched alcohol shown in the following Formula (6), and 132.2 parts of HMDI under the condition of Manufacturing Example A. This solid is defined as Associative thickener B.

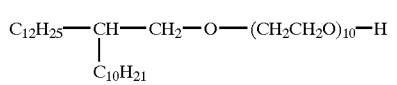
(6)

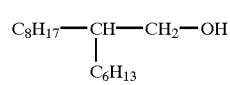
(10)

<Manufacturing Example C>

A light-yellow solid resultant was obtained from 580 parts of PEG 20000, 109 parts of EO 35 mols adduct of the branched alcohol shown in the following Formula (7), and 11.1 parts of tolylene diisocyanate (TDI) under the condition of Manufacturing Example A. This solid is defined as Associative thickener C.

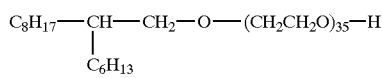
(7)

<Manufacturing Example D>

A light-yellow solid resultant was obtained from 360 parts of PEG 6000, 303 parts of a compound that 50 mols of EO was added to a secondary alcohol of $C_{11}$–$C_{14}$, and 122.2 parts of HMDI under the condition of Manufacturing Example A. This solid is defined as Associative thickener D.

<Manufacturing Example E>

A light-yellow solid resultant was obtained from 120 parts of PEG 2000, a compound that 100 mols of EO was added to a secondary alcohol of $C_{11}$–$C_{14}$, and 18.5 parts of tetramethylene diisocyanate under the condition of Manufacturing Example A. This solid is defined as Associative thickener E.

<Manufacturing Example F>

A light-yellow solid resultant was obtained from 550 parts of PEG 10000, 133 parts of EO 50 mols adduct of the branched alcohol shown in the following Formula (8), and 120.4 parts of HMDI under the condition of Manufacturing Example A. This solid is defined as Associative thickener F.

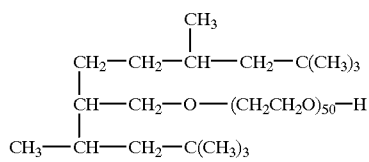
(8)

<Manufacturing Example G>

A light-yellow solid resultant was obtained from 367 parts of trimethylolpropane 100 EO adduct, 286 parts of EO 20 mols adduct of the branched alcohol shown in the following Formula (9), and 40.8 parts of HMDI under the condition of Manufacturing Example A. This solid is defined as Associative thickener G.

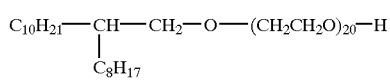
(9)

<Manufacturing Example H>

A light-yellow solid resultant was obtained from 288.2 parts of polyethylene glycol PEG-20000(molecular weight 20000), 7.0 parts of i-C16 alcohol shown in the following Formula (10), and 4.8 parts of hexamethylene diisocyanate HMDI under the condition of Manufacturing Example A. This solid is defined as Associative thickener H.

Constitutions of Associative thickener of Manufacturing Examples A–G is shown in FIG. 2.

The present inventors have conducted the following tests in order to study a fundamental property of these associative thickeners. Associative thickener A of the present invention, and carboxyvinyl polymer and xanthane gum were used, as the conventional water-soluble and cosmetically widely used polymer thickener.

Influence of Salt Concentration on Viscosity

The present inventors have examined how the viscosity (mPa·s, Brookfield viscometer, 25° C.) of the composition is changed. The composition is prepared by adding 0–2 wt % of NaCl to each solution of 1 wt % of Associative thickener A, 0.1 wt % of carboxyvinyl polymer, and 1 wt % of xanthane gum. The result is shown in Table 1.

TABLE 1

| NaCl amount/wt % | 0 | 0.1 | 0.5 | 1 | 2 |
|---|---|---|---|---|---|
| Associative thickener A | 3100 | 3240 | 3120 | 2960 | 2800 |
| Carboxyvinyl polymer | 3200 | 20 | 10 | 10 | 10 |
| Xanthane gum | 3400 | 12000 | 15250 | 17250 | 17000 |

It is understood from the result shown in Table 1 that the viscosity of Associative thickener solution does not depend on the amount of sodium chloride. To the contrary, it is understood that the viscosity of carboxyvinyl polymer is remarkably decreased while the viscosity of xanthane gum is remarkably increased due to addition of sodium chloride.

In next, the present inventors have examined the influence for viscosity affected by pH in the similar manner to the influence of salt.

Influence for Viscosity Affected by pH

Each solution of 1 wt % of Associative thickener A, 0.1 wt % of carboxyvinyl polymer, and 1 wt % of xanthane gum was adjusted to pH 4–8. Viscosity (mPa·s, Brookfield viscometer, 25° C.) of each solution was measured. The result is shown in Table 2.

TABLE 2

| PH | 4 | 5 | 6 | 7 | 8 |
|---|---|---|---|---|---|
| Associative thickener A | 2800 | 2810 | 3050 | 3100 | 3070 |
| Carboxyvinyl polymer | 100 | 2020 | 6250 | 8100 | 9900 |
| Xanthane gum | 3920 | 1980 | 3260 | 3800 | 4200 |

It is understood from the result shown in Table 2 that the viscosity of associative thickener solution is never affected by pH. To the contrary, it is understood that viscosity of carboxyvinyl polymer is decreased under low pH and viscosity of xanthane gum demonstrates complicated behavior.

In next, the present inventors have examined time stability of viscosity of said thickener.

Time Stability of Viscosity

Each solution of 1 wt % of Associative thickener A, 0.1 wt % of carboxyvinyl polymer, and 1 wt % of xanthane gum is preserved at 50° C. for 0 to 8 weeks. Change of viscosity (mPa·s, Brookfield viscometer, 25° C.) with time was measured. The result is shown in Table 3.

TABLE 3

| Preserved term/Week (50° C.) | 0 | 2 | 4 | 8 |
|---|---|---|---|---|
| Associative thickener A | 3200 | 1800 | 1010 | 840 |
| Carboxyvinyl polymer | 8150 | 8100 | 8100 | 7700 |
| Xanthane gum | 3800 | 3760 | 3600 | 3560 |

It is understood from the result shown in Table 3 that the viscosity of associative thickener tends to decrease with passage of time in the case where the composition is preserved at high temperature. To the contrary, it is understood that carboxyvinyl polymer and xanthane gum each is excellent in time stability of viscosity.

On the whole, it is understood from the result shown in Tables 1–3 that associative thickener in accordance with the cosmetic composition of the present invention has effects in stability of viscosity against external factor such as salt and pH, while it is inferior in time stability of viscosity at high temperature. To the contrary, it is understood that the viscosity of the conventional water-soluble polymer thickener such as carboxyvinyl polymer and xanthane gum is relatively excellent in time stability of viscosity while it is unstable due to external factor such as salt and pH.

Accordingly, the present inventors considered using water-soluble polymer thickener together with associative thickener in order to improve time stability of viscosity at high temperature that is the fault of associative thickener and conducted the following tests.

Time Stability of Viscosity Using Together with Water-Soluble Polymer Thickener

Each solution which mixed 0.1 wt % of carboxyvinyl polymer and 1 wt % of xanthane gum with 1 wt % of associative thickener was preserved at 50° C. for 0 to 8 weeks. Change of Viscosity (mPa·s, Brookfield viscometer, 25° C.) with time of each solution was measured. The result is shown in Table 4.

TABLE 4

| Preserved term/Week (50° C.) | 0 | 2 | 4 | 8 |
|---|---|---|---|---|
| Carboxyvinyl polymer + Associative thickener A | 5800 | 5800 | 5780 | 5720 |
| Xanthane gum + Associative thickener A | 6020 | 6000 | 5970 | 5900 |

It is understood from the result shown in Table 4 that time stability of viscosity of each solution is improved by mixing associative thickener with carboxyvinyl polymer or xanthane gum, which are water-soluble polymers.

In next, the present inventors have examined the influence for viscosity affected by salt in the case where associative thickener is mixed with the water-soluble polymer.

Influence for Viscosity Affected by Salt in the Case Where Associative Thickener is Mixed with Water-Soluble Polymer Thickener The water solutions which mixes 0.1 wt % of carboxyvinyl polymer and 1 wt % of xanthane gum with 1 wt % of associative thickener were prepared separately.

Change of viscosity (mPa·s, Brookfield viscometer, 25° C.) of each solution was measured with changing the amount of NaCl within 0–2 wt % in the similar manner to the above-mentioned test. The result is shown in Table 5.

TABLE 5

| NaCl amount/wt % | 0 | 0.1 | 0.5 | 1 | 2 |
|---|---|---|---|---|---|
| Carboxyvinyl polymer + Associative thickener A | 5800 | 4500 | 4220 | 4200 | 4120 |
| Xanthane gum + Associative thickener A | 6020 | 6800 | 7060 | 7120 | 7100 |

It is understood from the result shown in Table 5 that viscosity of each solution is hard to affect by addition of sodium chloride within the proper amount, even when associative thickener is mixed with carboxyvinyl polymer or xanthane gum, which is the water-soluble polymer.

In next, the present inventors have examined the influence for viscosity affected by pH in the case where associative thickener is mixed with the water-soluble polymer.

Influence for Viscosity Affected by pH in the Case Where Associative Thickener is Mixed with Water-Soluble Polymer Thickener The water solutions which mixes 0.1 wt % of carboxyvinyl polymer and 1 wt % of xanthane gum with 1 wt % of associative thickener were prepared separately.

Viscosity (mPa·s, Brookfield viscometer, 25° C.) of each composition was measured with changing pH 4–8 in the similar manner to the above-mentioned test. The result is shown in Table 6.

TABLE 6

| pH | 4 | 5 | 6 | 7 | 8 |
|---|---|---|---|---|---|
| Carboxyvinyl polymer + Associative thickener A | 3000 | 4800 | 5120 | 6510 | 7800 |
| Xanthane gum + Associative thickener A | 6200 | 6020 | 6540 | 6660 | 6800 |

From the result shown in Table 6, though it is observed that the viscosity of the system where associative thickener and carboxyvinyl polymer are mixed depends on pH, nevertheless the sufficient thickening effect can be observed even when the pH is small (pH 4). It is also understood that dependency to pH is not observed in viscosity of the system where associative thickener and xanthane gum are mixed and stable thickening behavior can be observed.

Accordingly, the present inventors have found the knowledge that the faults in time stability of viscosity at high temperature of associative thickener can be improved by mixing properly associative thickener with the water-soluble polymer thickener.

The present inventors have conducted four tests with respect to the compositions of various Working Examples and Test Examples mentioned in later in terms of usability, stability of viscosity and stability of emulsion in order to confirm its effect. Before describing various compositions, the content of them and evaluation method are described in the following. However, the other tests will be described in each time when the other tests have been conducted.

Test 1 Organolepic Test (moisture less stickiness)

An organoleptic test has been effected to 10 persons of professional panel by using the prepared sample. The result of evaluation will be shown as follows.

⊚: 8 or more among 10 person answered that the sample was favorable

○: or more among 10 person answered that the sample was favorable

Δ: 4 or more among 10 person answered that the sample was favorable

X: less than 4 among 10 person answered that the sample was favorable

Test 2 Salt Resistance Test of Viscosity

To the prepared sample was added 0.5% of sodium chloride solution and they were stirred and mixed. Salt resistance of viscosity was evaluated by measuring the viscosity before and after addition of salt at 25° C. The result of evaluation will be shown as follows.

⊚: decrease of viscosity was less than 10%

○: decrease of viscosity was less than 30%

Δ: decrease of viscosity was less than 50%

X: decrease of viscosity was 50% or more

Test 3 Temperature Stability Test of Viscosity

The prepared sample was preserved at 5° C. and 50° C. and the viscosity at each temperature was measured. Difference of viscosity between 5° C. and 50° C. is defined as temperature stability of viscosity. The result of evaluation will be shown as follows.

⊚: difference of viscosity was less than 10%

○: difference of viscosity was less than 30%

Δ: difference of viscosity was less than 50%

X: difference of viscosity was 50% or more

Test 4 Time Stability Test of Emulsion

Emulsification condition was observed after preserving the prepared sample at 50° C. The result of evaluation will be shown as follows.

○: no separation was observed

Δ: separation was slightly observed

X: two phased separation

The present inventors have conducted the test in order to use the characteristic association copolymer for a cosmetic composition. The basic compositions will be shown in Table 7. Test Examples 1, 2, and is the composition which include the associative thickener, carboxyvinyl polymer, xanthane gum, respectively. Test Examples 4 and 5 are the composition which mixes the associative thickener and the water-soluble polymer as the thickener.

TABLE 7

|  | Test Ex. 1 | Test Ex. 2 | Test Ex. 3 | Test Ex. 4 | Test Ex. 5 |
|---|---|---|---|---|---|
| Stearic acid | 2.0 | 2.0 | 2.0 | 2.0 | 2.0 |
| Cetyl alcohol | 1.5 | 1.5 | 1.5 | 1.5 | 1.5 |
| Petrolatum | 4.0 | 4.0 | 4.0 | 4.0 | 4.0 |
| Squalane | 5.0 | 5.0 | 5.0 | 5.0 | 5.0 |
| Triglyceryl-2-ethylhexanoate | 2.0 | 2.0 | 2.0 | 2.0 | 2.0 |
| Sorbitan monooleate | 2.0 | 2.0 | 2.0 | 2.0 | 2.0 |
| PEG 1500(*) | 3.0 | 3.0 | 3.0 | 3.0 | 3.0 |
| Triethanolamine | 1.0 | 1.0 | 1.0 | 1.0 | 1.0 |
| Methyl paraben | 0.2 | 0.2 | 0.2 | 0.2 | 0.2 |
| Perfume | 0.1 | 0.1 | 0.1 | 0.1 | 0.1 |
| Compound of Mfg. Ex. 1 | 1.0 | — | — | 1.0 | 1.0 |
| Carboxyvinyl Polymer | — | 0.1 | — | 0.1 | — |

TABLE 7-continued

|  | Test Ex. 1 | Test Ex. 2 | Test Ex. 3 | Test Ex. 4 | Test Ex. 5 |
|---|---|---|---|---|---|
| Xanthane Gum | — | — | 1.0 | — | 0.1 |
| Purified Water | Balance | Balance | Balance | Balance | Balance |
| Test 1: Organoleptic Test | ⊚ | Δ | Δ | ⊚ | ⊚ |
| Test 2: Salt Resistance of Viscosity | ⊚ | X | X | ⊚ | ⊚ |
| Test 3: Temp. Stability of Viscosity | ○ | ○ | Δ | ○ | ○ |
| Test 4: Time Stability of Emulsion | X | ○ | ○ | ○ | ○ |

*Polyethylene glycol 1500 (average molecular weight 1500), same in the following It is understood from the result shown in Table 7 that the compositions of Test Examples 1, 4 and 5 in accordance with the present invention are excellent in usability and salt resistance and temperature stability of viscosity. To the contrary, it is understood that the compositions of Test Examples 2 and 3, which were only used the conventional water-soluble as a thickener is inferior in usability and salt resistance of viscosity.

On the other hand, as for time stability of emulsion, Test Example 1 in accordance with the present invention is inferior, while Test Examples 2 and 3, which were only used the conventional water-soluble as a thickener and Test Examples 4 and 5, which mixes the associative thickener and the conventional thickener, are excellent. Accordingly, it is understood that using only the associative thickener has a problem in time stability of emulsion, in the case where a cosmetic composition is used for an oil-in-water emulsion composition.

One of the reason why the oil-in-water emulsion composition containing only the associative thickener is inferior in time stability of emulsion can be considered that the associative thickener mentioned hereinbefore is inferior in time stability of viscosity. However, the present inventors have further conducted the following tests so as to explore the other cause.

Viscosity of Shear Rate

The present inventors considered that the reason why the inferior stability of emulsion with associative thickener is due to the low viscosity at low shear rate. They were measured the viscosity where the shear rate of 0.1 wt % solutions of Associative thickener A, and carboxyvinyl polymer and xanthane gum, which are the water-soluble polymer is 0, 0.0001, 0.01 and 10 s$^{-1}$. The result is shown in Table 8.

TABLE 8

| Shear Rate (S$^{-1}$) | Associative thickener A | Carboxyvinyl polymer | Xanthane Gum |
|---|---|---|---|
| 0 | 5.1 | 17600 | 610 |
| 0.0001 | 5.1 | 3600 | 590 |
| 0.01 | 5.8 | 260 | 54 |
| 10 | 0.98 | 1.0 | 0.48 |

It is understood from the result of Table 8 that viscosity of associative thickener at low shear rate (0–0.01 S$^{-1}$) is considerably lower than the one of the conventional thickener. Therefore, the present inventors considered that the viscosity at low shear rate may affect particularly in time stability of emulsion. It is preferable to use associative thickener together with water-soluble polymers thickener in order to improve the stability of emulsion

Viscosity Ratio of Water-Soluble Polymer Thickener/Associative Thickener

The inventors found the knowledge that emulsion stability is improved by mixing the water-soluble polymer thickener and associative thickener have studied the preferred ratio of them. Evaluation of viscosity ratio is as follows. Salt resistance, temperature stability and time stability of emulsion are the same as shown in the foregoing Tests 2, 3, and 4, respectively.

First, the result of the mixture with carboxyvinyl polymer is shown in Table 9.

TABLE 9

|  | Test Ex. 6 | Test Ex. 7 | Test Ex. 8 | Test Ex. 9 | Test Ex. 10 | Test Ex 11 | Test Ex. 12 |
|---|---|---|---|---|---|---|---|
| Stearic acid | 2.0 | 2.0 | 2.0 | 2.0 | 2.0 | 2.0 | 2.0 |
| Cetyl alcohol | 1.5 | 1.5 | 1.5 | 1.5 | 1.5 | 1.5 | 1.5 |
| Petrolatum | 4.0 | 4.0 | 4.0 | 4.0 | 4.0 | 4.0 | 4.0 |
| Squalane | 5.0 | 5.0 | 5.0 | 5.0 | 5.0 | 5.0 | 5.0 |
| Triglyceryl-2-ethylhexanoate | 2.0 | 2.0 | 2.0 | 2.0 | 2.0 | 2.0 | 2.0 |
| Sorbitan monooleate | 2.0 | 2.0 | 2.0 | 2.0 | 2.0 | 2.0 | 2.0 |
| PEG 1500 | 3.0 | 3.0 | 3.0 | 3.0 | 3.0 | 3.0 | 3.0 |
| Triethanolamine | 1.0 | 1.0 | 1.0 | 1.0 | 1.0 | 1.0 | 1.0 |
| Methyl paraben | 0.2 | 0.2 | 0.2 | 0.2 | 0.2 | 0.2 | 0.2 |
| Perfume | 0.1 | 0.1 | 0.1 | 0.1 | 0.1 | 0.1 | 0.1 |
| Compound of Mfg. Ex. A | 3.0 | 2.0 | 2.0 | 1.0 | 1.0 | 0.5 | 0.3 |
| Carboxyvinyl Polymer | 0.01 | 0.01 | 0.02 | 0.05 | 0.1 | 0.1 | 0.1 |
| Purified Water | Balance | Balance | Balance | Balance | Balance | Balance | Balance |
| (Viscosity mPa · s) |  |  |  |  |  |  |  |
| Associative thickener A | 30000 | 11000 | 11000 | 3100 | 3100 | 200 | 50 |
| Carboxyvinyl polymer | 100 | 100 | 200 | 3000 | 8100 | 8100 | 8100 |
| Viscosity ratio (*) | 0.003 | 0.009 | 0.018 | 0.968 | 2.61 | 40.5 | 162 |
| Test 2: Salt Resistance of Viscosity | ◉ | ◉ | ◉ | ◉ | ◉ | ○ | Δ |
| Test 4: Time Stability of Emulsion | X | Δ | ○ | ○ | ○ | ○ | ○ |

*Viscosity of carboxyvinyl polymer/Viscosity of Associative thickener A

It is understood from the result of Table 9 that stability of emulsion can not be improved in the case where the viscosity ratio of carboxyvinyl polymer/associative thickener is less than about 0.01. On the other hand, it is understood that stability of viscosity is worse in the case where the viscosity ratio is more than about 100 because viscosity is largely changed according to change of salt concentration.

Then, the present inventors have studied about xanthane gum as the other water-soluble polymer.

TABLE 10

|  | Test Ex. 13 | Test Ex. 14 | Test Ex. 15 | Test Ex. 16 | Test Ex. 17 | Test Ex 18 | Test Ex. 19 |
|---|---|---|---|---|---|---|---|
| Stearic acid | 2.0 | 2.0 | 2.0 | 2.0 | 2.0 | 2.0 | 2.0 |
| Cetyl alcohol | 1.5 | 1.5 | 1.5 | 1.5 | 1.5 | 1.5 | 1.5 |
| Petrolatum | 4.0 | 4.0 | 4.0 | 4.0 | 4.0 | 4.0 | 4.0 |
| Squalane | 5.0 | 5.0 | 5.0 | 5.0 | 5.0 | 5.0 | 5.0 |
| Triglyceryl-2-ethylhexanoate | 2.0 | 2.0 | 2.0 | 2.0 | 2.0 | 2.0 | 2.0 |
| Sorbitan monooleate | 2.0 | 2.0 | 2.0 | 2.0 | 2.0 | 2.0 | 2.0 |
| PEG 1500 | 3.0 | 3.0 | 3.0 | 3.0 | 3.0 | 3.0 | 3.0 |
| Triethanolamine | 1.0 | 1.0 | 1.0 | 1.0 | 1.0 | 1.0 | 1.0 |
| Methyl paraben | 0.2 | 0.2 | 0.2 | 0.2 | 0.2 | 0.2 | 0.2 |
| Perfume | 0.1 | 0.1 | 0.1 | 0.1 | 0.1 | 0.1 | 0.1 |
| Compound of Mfg. Ex. A | 3.0 | 2.0 | 2.0 | 1.0 | 1.0 | 0.5 | 0.3 |
| Xanthane gum | 0.1 | 0.1 | 0.2 | 0.5 | 1.0 | 1.0 | 1.5 |
| Purified Water | Balance | Balance | Balance | Balance | Balance | Balance | Balance |
| (Viscosity mPa · s) |  |  |  |  |  |  |  |
| Associative thickener A | 30000 | 11000 | 11000 | 3100 | 3100 | 200 | 50 |
| Xanthane gum | 80 | 80 | 150 | 1000 | 3800 | 3800 | 6000 |
| Viscosity ratio | 0.003 | 0.007 | 0.014 | 0.32 | 1.23 | 19 | 132 |
| Test 2: Salt Resistance of Viscosity | ◉ | ◉ | ◉ | ◉ | ◉ | ○ | Δ |

TABLE 10-continued

|  | Test Ex. 13 | Test Ex. 14 | Test Ex. 15 | Test Ex. 16 | Test Ex. 17 | Test Ex 18 | Test Ex. 19 |
|---|---|---|---|---|---|---|---|
| Test 4: Time stability of emulsion | X | Δ | ○ | ○ | ○ | ○ | ○ |

*Viscosity of xanthane gum/Viscosity of Associative thickener A

It is understood from the result of Table 10 that stability of emulsion can not be improved sufficiently in the case where the viscosity ratio of xanthane gum/associative thickener is less than about 0.01. On the other hand, it is understood that stability of viscosity is worse in the case where the viscosity ratio is more than 100 because viscosity is largely changed according to change of salt concentration. Accordingly, judging from this result together with the above-mentioned result of carboxyvinyl polymer, it is preferable that the viscosity ratio of water-soluble polymer/associative thickener is about 0.01–100. Time stability of viscosity is excellent within the range of this ratio when carboxyvinyl polymer or xanthane gum is used as the water-soluble polymer.

In next, the present inventors have studied about the ingredient that can stabilize emulsification and can improve time stability of viscosity in addition to the water-soluble polymer.

Combination of Associative Thickener and Polyhydric Lower Alcohol

The present inventors have studied a combination of associative thickener and a polyhydric lower alcohol in addition to the water-soluble polymer.

To the oil-in-water emulsion composition of Test Example 1 was added 0–40 wt % of the following each polyhydric lower alcohol and time stability of viscosity and emulsion at 50% were examined. The preserved term was set at 0–8 weeks. The results in case of adding dipropylene glycol, glycerin, and 1,3-butylene glycol are shown in Tables 11, 12 and 13, respectively.

TABLE 11

Change of Viscosity (mPa · s) in Case of Adding Dipropylene Glycol

| Amount (wt %) | Preserved Term (weeks) | | | |
|---|---|---|---|---|
|  | 0 | 2 | 4 | 8 |
| 0 | 3200 | 1800 | 1010 | Separation to two phases |
| 0.05 | 3200 | 2060 | 1200 | Separation to two phases |
| 0.1 | 3160 | 2900 | 2630 | 2450 |
| 1 | 3150 | 3150 | 2980 | 2700 |
| 5 | 3100 | 3010 | 3050 | 2560 |
| 10 | 2900 | 2920 | 3000 | 2900 |
| 20 | 2560 | 2600 | 2560 | 2550 |
| 30 | 1880 | 1800 | 1820 | 1790 |
| 40 | 780 | 690 | 700 | 690 |

TABLE 12

Change of Viscosity (mPa · s) in Case of Adding Glycerin

| Amount (wt %) | Preserved Term (weeks) | | | |
|---|---|---|---|---|
|  | 0 | 2 | 4 | 8 |
| 0 | 3200 | 1800 | 1010 | Separation to two phases |
| 0.05 | 3220 | 1670 | 900 | Separation to two phases |
| 0.1 | 3100 | 2570 | 2320 | 2100 |
| 1 | 3160 | 2600 | 2480 | 2220 |
| 5 | 3300 | 2560 | 2220 | 2060 |
| 10 | 3260 | 3200 | 3300 | 3220 |
| 20 | 3010 | 3000 | 3020 | 3010 |
| 30 | 2770 | 2690 | 2700 | 2600 |
| 40 | 1140 | 1100 | 780 | 700 |

TABLE 13

Change of Viscosity (mPa · s) in Case of Adding 1,3-Butylene glycol

| Amount (wt %) | Preserved Term (weeks) | | | |
|---|---|---|---|---|
|  | 0 | 2 | 4 | 8 |
| 0 | 3200 | 1800 | 1010 | Separation to two phases |
| 0.05 | 3240 | 2730 | 2010 | Separation to two phases |
| 0.1 | 3190 | 3030 | 2830 | 2640 |
| 1 | 3220 | 3200 | 3010 | 2880 |
| 5 | 3210 | 3210 | 3200 | 3170 |
| 10 | 3180 | 3200 | 3200 | 3190 |
| 20 | 2980 | 2960 | 2960 | 2950 |
| 30 | 1900 | 1900 | 1890 | 1900 |
| 40 | 560 | 580 | 500 | 410 |

As shown in Tables 11–13, when the amount of the polyhydric lower alcohol is less than 0.1 wt %, every composition becomes unfavorable because thickening effect of associative thickener weaken and stickiness is occurred in the feeling of use.

Combination of Associative Thickener and Monohydric Lower Alcohol

In next, the present inventor has studied a combination of associative thickener and a monohydric lower alcohol. To the composition of Test Example 1 wad added 0–50 wt % of ethanol as the monohydric lower alcohol and stability of viscosity at 50° C. was examined. The reasult is shown in Table 14.

TABLE 14

Change of Viscosity (mPa · s) in Case of Adding Ethanol

| Amount (wt %) | Preserved Term (weeks) | | | |
|---|---|---|---|---|
| | 0 | 2 | 4 | 8 |
| 0 | 3200 | 1800 | 1010 | Separation to two phases |
| 0.05 | 3200 | 1820 | 1100 | Separation to two phases |
| 0.1 | 3190 | 2860 | 2530 | 2350 |
| 1 | 3120 | 3120 | 2880 | 2600 |
| 5 | 3300 | 3150 | 3200 | 3180 |
| 10 | 2850 | 2830 | 2830 | 2810 |
| 20 | 1860 | 1800 | 1820 | 1810 |
| 30 | 860 | 860 | 850 | 830 |
| 40 | 20 | 20 | 20 | 20 |
| 50 | 20 | 20 | 20 | 20 |

Monohydric lower alcohols such as ethanol generally decrease the viscosity of thickener. However, it is understood from the result of Table 14 that a combination of associative thickener and the monohydric lower alcohol unexpectedly has the effect for improving time stability of viscosity in the similar manner to the combination of associative thickener and polyhydric alcohol. Thickening effect can not be exhibited in the case where 40 wt % or more of ethanol is compounded. Also, it is difficult to improve stability of viscosity in the case where the amount of ethanol is less than 0.1 wt %. Accordingly, it is preferable that the amount of the monohydric lower alcohol is about 0.1–30 wt %.

Judging from the result shown hereinbefore, in the case where associative thickener is compounded as the cosmetic composition, it is preferred to combine with any of the water-soluble polymer, the polyhydric lower alcohol and the monohydric lower alcohol in view of time stability of viscosity. Also, if the cosmetic composition is the oil-in-water emulsion composition, it is preferred to combine the'same in view of time stability of emulsion.

In next, the present inventors have compared the concrete cosmetic composition in accordance with the present invention with the cosmetic composition of the prior art. The result is shown in Table 15. In Comparative Example 1, carboxyvinyl polymer, which conventionally used in the cosmetic was used instead of associative thickener.

TABLE 15

| Lotion | Working Example 1 | Comparative Example 1 |
|---|---|---|
| Stearic acid | 2.0 | 2.0 |
| Cetyl alcohol | 1.5 | 1.5 |
| Petrolatum | 4.0 | 4.0 |
| Squalane | 5.0 | 5.0 |
| Triglyceryl-2-ethylhexanoate | 2.0 | 2.0 |
| Sorbitan monooleate | 2.0 | 2.0 |
| PEG 1500 | 3.0 | 3.0 |
| Triethanolamine | 1.0 | 1.0 |
| Phenoxy ethanol | 0.2 | 0.2 |
| Perfume | 0.1 | 0.1 |
| Hydroxyethylcellulose | 0.3 | 0.3 |
| Compound of Mfg. Ex. A (viscosity ratio* = 0.11) | 1.0 | — |
| Carboxyvinyl polymer | — | 0.1 |
| Purified water | Balance | Balance |
| Test 1: Organoleptic test | ⊚ | Δ |
| Test 2: Salt resistance of viscosity | ⊚ | X |
| Test 3: Temperature stability of viscosity | ○ | Δ |
| Test 4: Stability of emulsion | ○ | ○ |

*Viscosity ratio = Hydroxyethylcellulose (320 mPa · s)/Associative thickener A (3000 mPa · s)

Manufacturing Method

Humectant and alkali were added to a part of purified water and the mixture was heated up and adjusted to 70° C. After dissolving the oily ingredient, surfactant, antiseptic and perfume were added thereto and the mixture was heated up and adjusted to 70° C. Thickener was dissolved into the rest of purified water. The oil phase was added to the water phase, which was prepared in advance. The mixture was preliminary emulsified and a solution of thickener was added thereto. After uniforming the emulsion particle by a homomixer, it was deaerated, filtered and cooled. Also, Test Examples mentioned hereinbefore are based on this Manufacturing Method.

It is understood from the result of Table 15 that the cosmetic composition, which includes associative thickener of the present invention is excellent in not only stability of viscosity (salt resistance and temperature stability on wide range), but also usability (moisture and less stickiness). On the other hand, it is found that the cosmetic composition of Comparative Example 1, which includes the conventional thickener, is inferior to the present invention in most tests.

Amount of Associative Thickener

In next, the present inventors have studied about the amount of associative thickener in the cosmetic composition in accordance with the present invention according to the following composition. The result is shown in Table 16.

TABLE 16

| Cleansing Foam | Test Ex. 19 | Test Ex. 20 | Test Ex. 21 | Test Ex. 22 | Test Ex. 23 | Test Ex. 24 |
|---|---|---|---|---|---|---|
| Stearic acid | 15 | 15 | 15 | 15 | 15 | 15 |
| Palmitic acid | 20 | 20 | 20 | 20 | 20 | 20 |
| Coconut oil | 2 | 2 | 2 | 2 | 2 | 2 |
| Potassium hydroxide | 6 | 6 | 6 | 6 | 6 | 6 |
| Glycerin | 15 | 15 | 15 | 15 | 15 | 15 |
| Polyethylene glycol 1500 | 10 | 10 | 10 | 10 | 10 | 10 |
| Glyceryl monostearate | 2 | 2 | 2 | 6 | 6 | 6 |

TABLE 16-continued

| Cleansing Foam | Test Ex. 19 | Test Ex. 20 | Test Ex. 21 | Test Ex. 22 | Test Ex. 23 | Test Ex. 24 |
|---|---|---|---|---|---|---|
| POE (20) sorbitan Monostearate | 2 | 2 | 2 | 2 | 2 | 2 |
| Associative thickener B | 0.001 | 0.01 | 0.1 | 5 | 10 | 15 |
| Carboxyvinyl polymer | 0.05 | 0.05 | 0.05 | 0.05 | 0.05 | 0.05 |
| Phenoxy ethanol | 0.2 | 0.2 | 0.2 | 0.2 | 0.2 | 0.2 |
| Chelating agent | q.s. | q.s. | q.s. | q.s. | q.s. | q.s. |
| Purified Water | Balance | Balance | Balance | Balance | Balance | Balance |
| (Viscosity mPa · s) | | | | | | |
| Associative thickener B | 20 | 40 | 120 | 58000 | 167000 | 560000 |
| Carboxyvinyl polymer | 3000 | 3000 | 3000 | 3000 | 3000 | 3000 |
| Viscosity ratio (*) | 150 | 75 | 25 | 0.052 | 0.018 | 0.005 |
| Test 1: Organoleptic Test | Δ | ○ | ⊚ | ⊚ | ○ | Δ |

*Viscosity ratio = Viscosity of carboxyvinyl polymer/Viscosity of Associative thickener B

Manufacturing Method

Fatty acid, emollient, humectant and antiseptic were heated and dissolved and the mixture was maintained at 70° C. Purified water dissolved alkali in advance was added to the oil phase which was stirred. After addition, the temperature of the mixture was kept at 70° C. for a period time and neutralizing reaction was terminated. Then, surfactant, chelating agent and thickener dissolved in advance was added thereto and stirred and mixed. After deaeration and filtration, the mixture was cooled.

It is understood from the result of Table 16 that the amount of associative thickener included in the cosmetic composition of the present invention is preferably 0.01–10 wt % and more preferably is 0.1–5 wt %. If the amount of associative thickener is more than 10 wt %, usability is spoiled because stickiness is occurred. On the other hand, not only the effect as the thickener is spoiled but also moisture feeling is inferior in usability even no stickiness, in the case where the amount of associative thickener is less than 0.01 wt %.

Working Examples will be shown in the following Needless to say, however, the present invention is not restricted to these Working Examples, The amount is shown by wt %

TABLE 17

| Working Example 2 | Skin Lotion | |
|---|---|---|
| Humectant | Sorbitol | 4.0 |
| | Dipropylene glycol | 6.0 |
| | PEG 1500 | 5.0 |
| Surfactant | POE (20) Oleylalcoholether | 0.5 |
| Water-soluble polymer | Carboxyvinyl polymer (Pemulen TR-2, manufactured by Goodrich Corp.) | 0.05 |
| Associative thickener | Compound of Manufacturing Example C | 0.1 |
| Alcohol | Ethanol | 10.0 |
| Antiseptic | Methyl paraben | 0.2 |
| Perfume | | q.s. |
| Chelating agent | | q.s. |
| Buffering agent | | q.s. |
| Purified water | | Balance |

*Viscosity ratio = Carboxyvinyl polymer (780 mPa · s)/Associative thickener C (150 mPa · s)

Manufacturing Method

Chelating agent was dissolved into a part of purified water. A viscous solution was prepared by mixed and stirred thereto. Humectant and buffering agent were added to the rest of purified water and dissolved under room temperature. The viscous solution prepared in advance was added thereto, and a uniform solution was obtained. An alcohol solution was obtained by adding antiseptic, surfactant, and perfume to ethanol and it was solubilized by adding to and mixing with the above-mentioned uniform solution.

TABLE 18

| Working Example 3 | Emollient Lotion | |
|---|---|---|
| Oily ingredient | Cetyl alcohol | 1 |
| | Beeswax | 0.5 |
| | Petrolatum | 2 |
| | Squalane | 6 |
| | Dimethylpolysiloxane | 2 |
| Alcohol | Ethanol | 5 |
| Humectant | Glycerin | 4 |
| | 1,3-Butylene glycol | 4 |
| Surfactant | POE (10) monooleate | 1 |
| | Glyceryl monostearate | 1 |
| Associative thickener | Compound of Manufacturing Example D | 2 |
| Water-soluble polymer | Agar (viscosity ratio* = 0.011) | 0.1 |
| Antiseptic | Methyl paraben | 0.2 |
| Purified water | | Balance |

*Viscosity ratio = Agar (200 mPa · s)/Associative thickener D (18000 mPa · s)

Manufacturing Method

Humectant was added to purified water and the mixture was heated up to 70° C. Surfactant and antiseptic were added to the oily ingredients and the mixture was heated up to 70° C. Preliminary emulsification was effected by adding the latter to the former. Thickener and ethanol were added thereto and stirred. After uniforming the emulsion particle by a homomixer, it was, deaerated, filtered and cooled.

TABLE 19

| Working Example 4 | Emollient Cream | |
|---|---|---|
| Oily ingredient | Cetyl alcohol | 5 |
| | Stearic acid | 3 |
| | Petrolatum | 5 |
| | Squalane | 10 |
| | Dimethylpolysiloxane | 2 |
| | Triglyceryl-2-ethylhexanoate | 7 |
| Humectant | Dipropylene glycol | 5 |
| | Glycerin | 5 |
| Surfactant | Propyleneglycol monostearate | 3 |
| | POE (20) cetylalcoholether | 3 |

TABLE 19-continued

| Working Example 4 | Emollient Cream | |
|---|---|---|
| Alkali | Triethanolamine | 1 |
| Associative thickener | Compound of Manufacturing Example E | 3 |
| Water-soluble polymer | Hydroxyethylcellulose (Natrosol plus 330, manufactured by Hercules Inc.) (viscosity ratio* = 0.138) | 1 |
| Antiseptic | Phenoxy ethanol | 0.2 |
| Antioxidant | Ionol | 0.1 |
| Perfume | | q.s. |
| Purified water | | Balance |

*Viscosity ratio = Hydroxyethylcellulose (3200 mPa · s)/Associative thickener E (23200 mPa · s)

Manufacturing Method

Humectant, alkali, and thickener were added to purified water and the mixture was heated up to 70° C. After heating and dissolving the oily ingredients, surfactant, antiseptic, antioxidant, and perfume were added thereto and the mixture was heated up to 70° C. Preliminary emulsification was effected by adding the latter to the former. After uniforming the emulsion particle by a homomixer, it was deaerated, filtered and cooled.

TABLE 20

| Working Example 5 | Moisture Gel | |
|---|---|---|
| Humectant | Dipropylene glycol | 7 |
| | PEG 1500 | 8 |
| Associative thickener | Compound of Manufacturing Example F | 1 |
| Water-soluble polymer | Cationized Cellulose (Catinal PC-100, manufactured by Toho Chemical Industry Co., Ltd.) | 0.4 |
| | Methylcellulose (viscosity ratio* = 15) | 0.2 |
| Alkali | Potassium hydroxide | 0.1 |
| Antiseptic | Methyl paraben | q.s. |
| Chelating agent | | q.s. |
| Perfume | | q.s. |
| Purified water | | Balance |

*Viscosity ratio = Cationized Cellulose + Methylcellulose (34600 mPa · s)/Associative thickener F (2300 mPa · s)

Manufacturing Method

After dissolving associative thickener and water-soluble polymer into purified water in uniform, PEG 1500 and chelating agent were added thereto. Surfactant was added to dipropylene glycol and the mixture was heated and dissolved at 50° C. Then, antiseptic and perfume were added thereto. The former prepared in advance was slowly added to the latter with stirring. Alkali solution was added thereto and the mixture was sufficiently stirred for neutralization,

TABLE 21

| Working Example 6 | Essence | |
|---|---|---|
| Humectant | Sorbitol | 8.0 |
| | 1,3-Butylene glycol | 5.0 |
| | PEG 1500 | 7.0 |
| | Hyaluronic acid | 0.1 |
| Alcohol | Ethanol | 7.0 |
| Surfactant | POE oleyl alcohol ether | 1.0 |

TABLE 21-continued

| Working Example 6 | Essence | |
|---|---|---|
| Associative thickener | Compound of Manufacturing Example G (viscosity ratio* = 2.26) | 0.5 |
| Antiseptic | Phenoxyethanol | 0.2 |
| Perfume | | q.s. |
| Buffering agent | | q.s. |
| Purified water | | Balance |

*Viscosity ratio = Hyaluronic acid (2600 mPa · s)/Associative thickener G (1150 mPa · s)

Manufacturing Method

Humectant, buffering agent, and thickener were added to purified water and the mixture was dissolved under room temperature. After dissolving surfactant, emollient, perfume, and antiseptic into ethanol, it was solubilized to the former water phase.

TABLE 22

| Working Example 7 | Pack | |
|---|---|---|
| Film-forming agent | Polyvinyl alcohol | 15 |
| Associative thickener | Compound of Manufacturing Example A (viscosity ratio* = 2.92) | 5 |
| Humectant | 1,3-Butylene glycol | 5 |
| Surfactant | POE oleyl alcohol ether | 0.5 |
| Alcohol | Ethanol | 12 |
| Antiseptic | Methyl paraben | 0.2 |
| Perfume | | q.s. |
| Buffering agent | | q.s. |
| Purified water | | Balance |

*Viscosity ratio = Polyvinyl alcohol (48000 mPa · s)/Associative thickener A (140000 mPa · s)

Manufacturing Method

Buffering agent and humectant were added to purified water and the mixture was heated up to 70° C. Thickener and film-forming agent were added thereto and the mixture was dissolved while stirring. Perfume, antiseptic, and surfactant were added to ethanol. After dissolution, the latter was solubilized to the former water phase.

TABLE 23

| Working Example 8 | Liquid Foundation | |
|---|---|---|
| Powder | Talc | 3 |
| | Titanium dioxide | 5 |
| | Red iron oxide | 0.5 |
| | Yellow iron oxide | 1.4 |
| | Black iron oxide | 0.1 |
| Water Phase | Bentonite | 0.5 |
| | POE sorbitan monostearate | 0.9 |
| | Triethanolamine | 1 |
| | Propyleneglycol | 10 |
| | Associative thickener B | 0.5 |
| | Carageenan (viscosity ratio* = 0.539) | 0.1 |
| | Purified water | Balance |
| Oil Phase | Stearic acid | 2.2 |
| | Isohexadecyl alcohol | 7 |
| | Glyceryl monostearate | 2 |
| | Liquid lanolin | 2 |
| | Liquid paraffin | 8 |
| Antiseptic | | q.s. |
| Perfume | | q.s. |

*Viscosity ratio = Carageenan (550 mPa · s)/Associative thickener B (1020 mPa · s)

Manufacturing Method

The oil phase and the water phase each was heated up to 70° C. and dissolved separately. The oil phase and the powder were added to the water phase. After emulsifying the mixture by a homomixer, antiseptic and perfume were added thereto. The mixture was cooled while stirring.

TABLE 24

| Working Example 9 | Nail Enamel | |
|---|---|---|
| Resin | Polymer emulsion (*) | 85.0 |
| Plasticizer | Diisobutyl adipate | 4.0 |
| Film-forming assistant | Carbitol | 4.0 |
| Antiseptic | Methyl paraben | 0.2 |
| Defoaming agent | | q.s. |
| Pigment | Red No. 220 | 0.3 |
| | Titanium oxide | 0.2 |
| Associative thickener | Compound of Manufacturing Example C | 0.2 |
| Ion-exchanged water | | 6.1 |

(*) Daitozole 5000A-S (manufactured by Daito Chemical Industrial Corporation)

Manufacturing Method

The associative thickener was added to ion-exchanged water and the mixture was heated and dissolved. The mixture was added to polymer emulsion. Diisobutyl adipate and carbitol were slowly added thereto and the other ingredients were also added to the mixture. After dispersing the mixture in uniform, it was deaerated.

TABLE 25

| Working Example 10 | Shampoo | |
|---|---|---|
| Surfactant | Sodium lauryl POE sulfate ester | 9 |
| | Amide propylbetaine myristate | 3 |
| | Coconut fatty acid diethanolamide | 4 |
| Humectant | Glycerin | 1 |
| Water-soluble polymer | Cationized Cellulose (Quatrisoft LM-200, manufactured by Amercol Corp.) | 0.2 |
| Associative thickener | Compound of Manufacturing Example D (viscosity ratio* = 0.214) | 2 |
| Perfume | | q.s. |
| Coloring agent | | q.s. |
| Antiseptic | | q.s. |
| Sequestering agent/ pH adjustor | | q.s. |
| Purified water | | Balance |

*Viscosity ratio = Cationized cellulose (1200 mPa · s)/Associative thickener D (5600 mPa · s)

Manufacturing Method

Purified water was heated up to 70° C. The other ingredients were added thereto and dissolved in uniform. Then the mixture was cooled.

TABLE 26

| Working Example 11 | Rinse | |
|---|---|---|
| Oily ingredient | Silicone oil | 3 |
| | Liquid paraffin | 1 |
| | Cetyl alcohol | 1.5 |
| | Stearyl alcohol | 1 |
| | Stearyltrimethyl ammonium chloride | 0.7 |
| Humectant | Glycerin | 3 |
| Associative thickener | Compound of Manufacturing Example E | 0.5 |
| Water-soluble polymer | Poly (diallyidimethylammonium chloride) (Marqart 100, manufactured by Calgon Corp.) (viscosity ratio* = 0.82) | 0.5 |
| Perfume, Coloring | | q.s. |

TABLE 26-continued

| Working Example 11 | Rinse | |
|---|---|---|
| agent, Antiseptic | | |
| Purified water | | Balance |

*Viscosity ratio = Poly (diallyldimethylammonium chloride) (820 mPa · s)/Associative thickener E (1000 mPa · s)

Manufacturing Method

The associative thickener, water-soluble polymer, stearyltrimethyl ammonium chloride, glycerin, and coloring agent were added to purified water and the mixture was kept at 70° C. (Water phase). The other ingredients were mixed and the mixture was heated, dissolved and kept at 70° C. (Oil Phase). Oil phase was added to water phase and the mixture was emulsified by a homomixer. Then, it was cooled while stirring.

TABLE 27

| Working Example 12 | Hair Gel | |
|---|---|---|
| Water-soluble polymer | Acrylic resin alkanolamine solution | 2 |
| Associative thickener | Compound of Manufacturing Example F (viscosity ratio* = 0.019) | 2 |
| Humectant | Glycerin | 5 |
| Alcohol | Ethanol | 20 |
| Surfactant | POE octyl dodecyl ether | 1 |
| Perfume, Chelating agent | | q.s. |
| Purified water | | Balance |

*Viscosity ratio = Acrylic resin alkanolamine solution (480 mPa · s)/Associative thickener F (25000 mPa · s)

Manufacturing Method

A part of purified water was added to associative thickener and glycerin and the mixture was heated and dissolved at 70° C. The other ingredients were added to the rest of purified water and the mixture was dissolved while stirring.

TABLE 28

| Working Example 13 | Sun Screen | |
|---|---|---|
| Oil Phase | Octyl p-methoxycinnamate | 3 |
| | Isopropyl myristate | 2 |
| | Oleyl oleate | 4 |
| | Petrolatum | 1 |
| | Stearyl alcohol | 2 |
| | Stearic acid | 2 |
| | Glyceryl monostearate | 2 |
| | Vitamin E acetate | 0.05 |
| | Antiseptic, Perfume | q.s. |
| Water Phase | 1,3-Butylene glycol | 5 |
| | Associative thickener H | 1 |
| | Polyacrylamide (viscosity ratio* = 0.276) | 0.4 |
| | Purified water | Balance |

*Viscosity ratio = Polyacrylamide (1880 mPa · s)/Associative thickener H (6800 mPa · s)

Manufacturing Method

The oil phase and the water phase each was heated up to 70° C. and dissolved separately. The oil phase was added to the water phase. After emulsifying the mixture by a homogenizer, it was cooled down by a heat exchanger.

In next, the sample prepared by Working Examples 1–13 was tested according to Tests 1–3 mentioned hereinbefore. The result is shown in Table 29. Test 4 was also tested in the oil-in-water emulsion composition. Carboxyvinyl polymer, which was relatively excellent as the thickener for the conventional cosmetic was used for preparing the composition of Comparative Examples 1–13 instead of associative thickeners of Working Examples 1–13. The methods for manufacturing the sample of Comparative Examples are based on each Working Examples.

TABLE 29

|     | Working Examples |        |        |        | Comparative Examples |        |        |        |
|-----|------|------|------|------|------|------|------|------|
| No. | Test 1 | Test 2 | Test 3 | Test 4 | Test 1 | Test 2 | Test 3 | Test 4 |
| 1   | ⊚ | ⊚ | ○ | ○ | Δ | X | X | ○ |
| 2   | ○ | ⊚ | ⊚ | — | Δ | Δ | Δ | — |
| 3   | ○ | ⊚ | ○ | ○ | X | X | X | ○ |
| 4   | ⊚ | ⊚ | ⊚ | ⊚ | ○ | Δ | X | X |
| 5   | ⊚ | ⊚ | ○ | — | Δ | X | Δ | — |
| 6   | ⊚ | ⊚ | ⊚ | — | X | X | Δ | — |
| 7   | ○ | ⊚ | ⊚ | — | X | X | X | — |
| 8   | ⊚ | ⊚ | ⊚ | ○ | Δ | Δ | X | ○ |
| 9   | ⊚ | ⊚ | ⊚ | — | X | X | X | — |
| 10  | ⊚ | ⊚ | ○ | — | Δ | X | X | — |
| 11  | ⊚ | ⊚ | ○ | ○ | X | X | X | ○ |
| 12  | ○ | ⊚ | ⊚ | — | Δ | X | Δ | — |
| 13  | ○ | ⊚ | ⊚ | ○ | Δ | X | X | ○ |

Test 1: Organoleptic Test (moisture feeling, less stickiness)
Test 2: Test for Salt Resistance of Viscosity
Test 3: Test for Temperature Stability of Viscosity
Test 4: Test for Time Stability of Emulsion It is found from the result of Table 29 that the cosmetic preparation using associative thickener of the present invention exhibits excellence in every respect such as usability and stability of viscosity as compared with the cosmetic composition of the prior art using carboxyvinyl polymer. Time stability of emulsion is favorable in every Working Examples in the oil-in-water emulsion composition of the present invention.

In addition to this, the present inventors have found the knowledge as mentioned hereinafter.

Viscosity Improving Effect by Surfactant

The present inventors have studied the relation between associative thickener of the present invention and surfactant in the system where no oily ingredients are existed. The present inventors have studied the combination (viscosity under coexistence with 1 wt % of associative thickener) of associative thickener (Compound of Manufacturing Example E) and surfactant.

First, the relation of sodium lauryl sulfate, which is an anionic surfactant and associative thickener, was studied.

The result is shown in Table 30.

TABLE 30

Anionic surfactant (Sodium lauryl sulfate)

| Concentration of surfactant (mmol/L) | 0 | 1 | 5 | 10 | 50 | 100 |
|---|---|---|---|---|---|---|
| Concentration of surfactant (wt %) | 0 | 0.03 | 0.14 | 0.29 | 1.44 | 2.88 |
| Viscosity (mPa · s) | 3000 | 3900 | 19200 | <50 | <50 | <50 |

It is understood from Table 30 that the concentration of the anionic surfactant is preferable within the range that is less than about five times of cmc (critical micellar concentration) with respect to 1 wt % of associative thickener in the system where no oily ingredient exist because cmc (critical micellar concentration) of sodium lauryl sulfate is about 8 mmol/L. However, an upper limit of the concentration of surfactant is proportional to the concentration of associative thickener. Namely the range within less than ten times of cmc is preferable with respect to 2 wt % of associative thickener. The same thing applies to the cationic and amphoteric surfactants. This phenomenon can be found from FIG. 3 mentioned hereinafter.

In next, the relation of lauryl trimethyl ammonium chloride, which is a cationic surfactant and associative thickener, is shown in Table 31.

TABLE 31

Cationic surfactant (Lauryl trimethyl ammonium chloride)

| Concentration of surfactant (mmol/L) | 0 | 1 | 5 | 10 | 50 | 100 |
|---|---|---|---|---|---|---|
| Concentration of surfactant (wt %) | 0 | 0.03 | 0.13 | 0.26 | 1.32 | 2.64 |
| Viscosity (mPa · s) | 3000 | 5850 | 7700 | 14200 | <50 | <50 |

It is understood from Table 31 that the concentration of the cationic surfactant is preferable within the range that is less than about five times of cmc (critical micellar concentration) with respect to 1 wt % of associative thickener in the system where no oily ingredient exist because cmc (critical micellar concentration) of lauryl trimehtyl ammonium chloride is about 14 mmol/L.

In next, the relation of polyoxyethylene (7) laurylether, which is a nonionic surfactant whose HLB is 10.9 and associative thickener, is shown in Table 32.

TABLE 32

| Nonionic surfactant | HLB 10.9 (POE (7) laurylether) | | | | | | | |
|---|---|---|---|---|---|---|---|---|
| Concentration of surfactant (mmol/L) | 0 | 0.01 | 0.1 | 1 | 5 | 10 | 50 | 100 |
| Concentration of surfactant (wt %) | 0 | 0.0005 | 0.005 | 0.05 | 0.24 | 0.49 | 2.39 | 4.78 |
| Viscosity (mPa · s) | 3000 | 3950 | 2750 | 4700 | 18000 | 34800 | 3050 | 1450 |

It is understood from Table 32 that the concentration of the nonionic surfactant whose HLB is 12 or less is preferable within the range that is 5 wt % or less with respect to 1wt % of associative thickener in the system where no oily ingredient exist.

In next, the relation of polyoxyethylene (15) laurylether, which is a nonionic surfactant whose HLB is 14.1 and associative thickener, is shown in Table 33.

TABLE 33

| Nonionic surfactant | HLB 14.1 (POE (15) laurylether) | | | | | | | |
|---|---|---|---|---|---|---|---|---|
| Concentration of surfactant (mmol/L) | 0 | 0.01 | 0.1 | 1 | 5 | 10 | 50 | 100 |
| Concentration of surfactant (wt %) | 0 | 0.00083 | 0.0083 | 0.083 | 0.415 | 0.83 | 4.15 | 8.3 |
| Viscosity (mPa · s) | 3000 | 2960 | 3300 | 6800 | 42400 | 32000 | <50 | <50 |

It is understood from Table 33 that the concentration of the nonionic surfactant whose HLB is 15 or less is preferable as a cosmetic composition within the range that is 2 wt % or less with respect to 1 wt % of associative thickener in the system where no oily ingredient exist. Also, in the case where HLB of the nonionic surfactant is more than 15, the preferable concentration of the nonionic surfactant is 1 wt % or less.

Also, it is found that the preferable range of the concentration of the surfactant in the case where 40 wt % or less of the oily ingredients is included in the cosmetic composition as follows. If the nonionic surfactant whose HLB is 12 or less, the nonionic surfactant whose HLB is 15 or less, the nonionic surfactant whose HLB is 15 and the ionic surfactant, the concentration of the surfactant is preferable within the range of 10 wt % or less, 8 wt % or less, 6 wt % of less and ten times or less of cmc (critical micellar concentration) with respect to 0.1 to 5 wt % of associative thickener, respectively. Namely, a large amount of the surfactant within the rate that the surfactant is spent for emulsification can be compounded into the cosmetic composition in the case where the oily ingredient is compounded.

Accordingly, it is understood that associative thickener of the present invention produces remarkable thickening effect by existence of the proper amount of surfactants. FIG. 3 is an explanatory drawing of this thickening mechanism. Namely, cross-linking points are increased with forming a mixing micelle of surfactant and associative thickener by addition of the proper amount of surfactant. Accordingly viscosity of associative thickener in accordance with the present invention is further increased. However, viscosity will be decreased in the case where the surfactant is compounded over the proper amount because a hydrophobic group is saturated and cross-linking points are decreased.

As a result of diligent studies based on the above-mentioned thickening mechanism, the present inventors have found the following knowledge. Remarkable thickening function can be observed in the case where a micelle of the surfactant is 2 or less with respect to one molecule of associative thickener in the system where associative thickener coexists with the surfactant. Namely, the present inventors have found it is effective as the cosmetic composition in the case where the ratio of molar concentration $C_p$ of associative thickener and molar concentration $C_m$ of surfactant micelle is 1:2 or less despite of the type of surfactants. In here, $C_m$ will be shown as follows.

$C_m = (C_s - cac)/N'_{agg}$ $C_m$: Molar concentration of micelle
$C_s$: Molar concentration of surfactant monomer
cac: Critical concentration that surfactant forms micelle under coexistence of Associative thickener
$N'_{agg}$: Association number of micelle of surfactant under coexistence of association thickener Next, the present inventors have studied about the effect of using associative thickener together with humectants.

Improvement of Moisturizing Function

Improvement of moisturizing retention function of skin was evaluated with measurement of conductance. Associative thickener C was and was not added to a skin lotion (formulation in Table 34), which contained glycerin and dipropylene glycol as a humectant. Conductance of skin in both cases was compared. Namely, conductance of skin in the chest before processing with sample and after 1 hour and 24 hours of processing sample was measured. Improvement of moisturizing retention function was judged from this changing rate. It is possible to study the effect for water absorption properties of horny layer and water retention function with changing rate of conductance of skin. If the changing rate is high, it is not preferable in view of reduction of water in horny layer. Changing rate of conductance conductance after processing/conductance before processing The result is shown in Table 34.

TABLE 34

| Component | Comp. Ex. 14 | Comp. Ex. 15 | Work. Ex. 14 |
|---|---|---|---|
| Glycerin | 5 | — | 5 |
| Dipropylene glycol | 5 | — | 5 |
| POE (20) oleyl alcohol ether | 0.5 | 0.5 | 0.5 |
| Associative thickener C | — | 1 | 1 |
| Ethanol | 5 | 5 | 5 |
| Methyl paraben | 0.2 | 0.2 | 0.2 |
| Perfume | q.s. | q.s. | q.s. |
| Purified water | Balance | Balance | Balance |
| Change rate of conductance | 0.54 ± 0.05 | 0.31 ± 0.03 | 0.86 ± 0.06 |

As a result of Table 34, Working Example 14 which contains associative thickener and humectant remarkably inhibits the change of conductance of skin and can improve water retention function as compared with Comparative Examples 14 and 15, which does not contain associative thickener and humectant, respectively In next, the present inventors have studied about the effect of using associative thickener together with pharmaceuticals as the application of the composition in accordance with the present invention.

Percutaneous Absorption Promoting Effect

α-Hydroxy acid such as lactic acid have the effect for separating old horny layer and making skin smooth and soft. Associative thickener A mentioned hereinbefore was and was not added to a cream (formulation in Table 35), which contained 5 wt % of lactic acid. Skin transparency in both cases was compared. These tests were effected with using in vitro standard Frantz type percutaneous diffusion cell and resected skin of swine (described in the following document: T. J.Franz, J.Invest.Dermatol.,64:190–195(1975)).

TABLE 35

| Component | Comp. Ex. 16 | Work. Ex. 15 |
| --- | --- | --- |
| Cetyl alcohol | 2.5 | 2.5 |
| Stearic acid | 1.5 | 1.5 |
| Petrolatum | 2 | 2 |
| Squalane | 5 | 5 |
| Dipropylene glycol | 5 | 5 |
| Glycerin | 5 | 5 |
| POE (20) cetyl alcohol ether | 3 | 3 |
| Triethanolamine | 0.5 | 0.5 |
| Associative thickener A | — | 2 |
| Phenoxy ethanol | 0.2 | 0.2 |
| Lactic acid | 5 | 5 |
| Perfume | q.s. | q.s. |
| Purified water | Balance | Balance |

Figure 4:
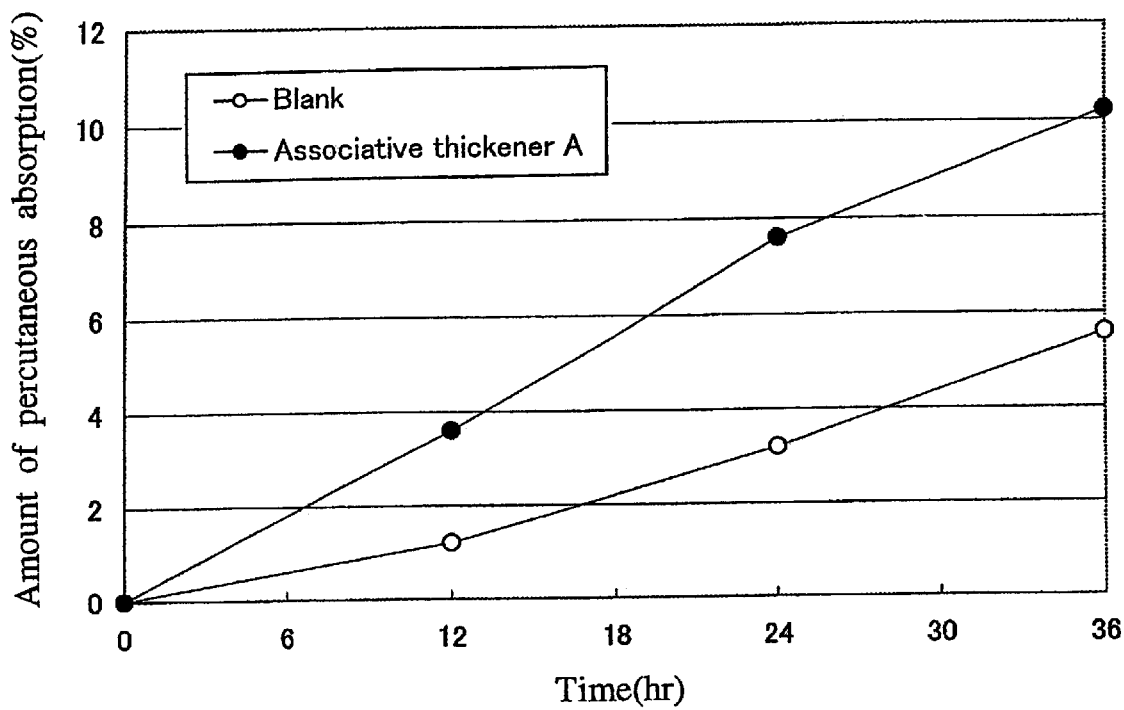
FIG. 4 shows percutaneous absorption promoting effect of the pharmaceutical in the cosmetic composition of the present invention.

As is clear from FIG. 4, it is understood that the cream of Working Example 15, which includes Associative thickener A can improve skin transparency with lactic acid as compared with the one of Comparative Example 16, which does not include associative thickener.

Irritation Relaxation Effect

α-Hydroxy acid is known to have the effect for separating old horny layer and making skin smooth and soft as mentioned hereinbefore. However, if a preparation which contains α-hydroxy acid is applied to the skin, it smarts in a part and sometimes causes irritations such as reddish of skin. A cream, which includes 1 to 10 wt % of lactic acid was prepared in the similar manner to Working Examples mentioned hereinbefore and the influence on skin irritation was examined with patch test on the case with or without the above-mentioned Associative thickener B. 0.3 mL of the preparation was pasted on the back of panelist. After 24 hours, the patch was removed and professional estimator marked irritation.

Figure 5:
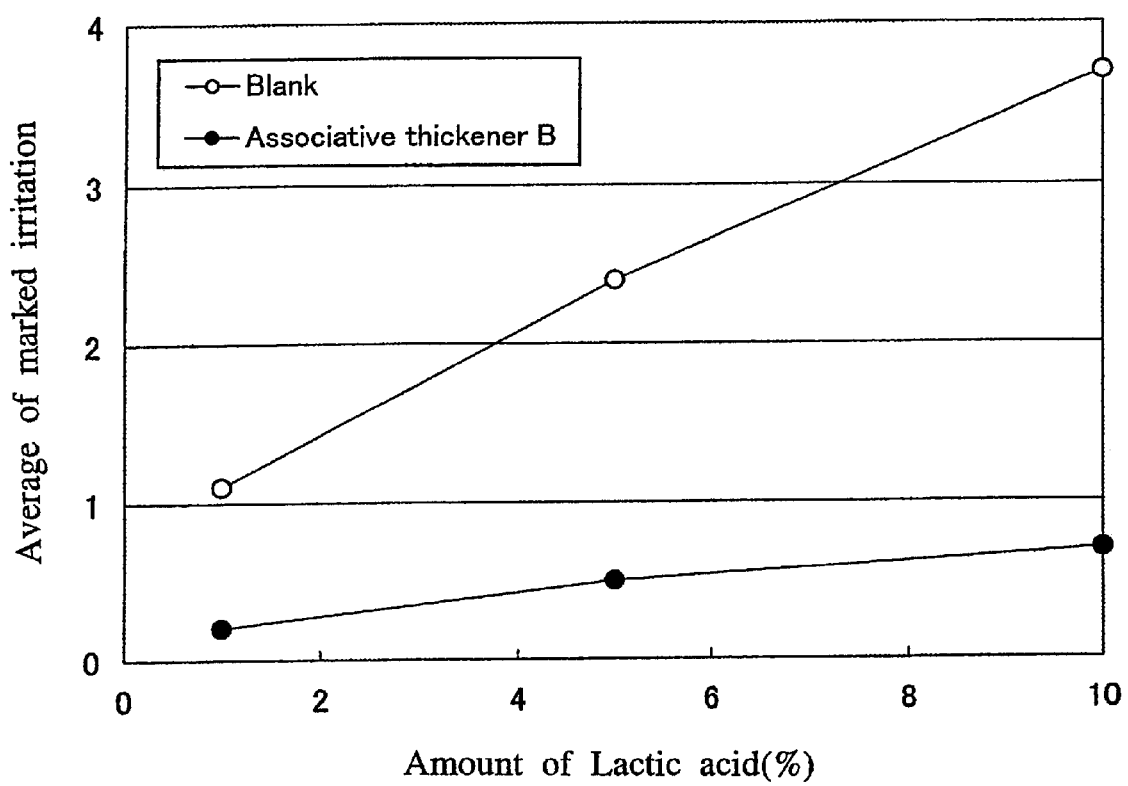
FIG. 5 shows irritation relaxation effect of the cosmetic composition of the present invention.

As is clear from FIG. 5, it is found that the preparation which includes Associative thickener B decrease skin irritation caused by lactic acid as compared with the preparation which does not include associative thickener.

As explained hereinbefore, the cosmetic composition of the present invention is excellent in stability of viscosity and usability by compounding a specific associative thickener into the cosmetic composition. Also, the cosmetic composition of the present invention can improve time stability of viscosity at high temperature by using the associative thickener together with a water-soluble polymer, a polyhydric lower alcohol and a monohydric lower alcohol. Further, time stability of emulsion can be improved by using associative thickener together with the water-soluble polymer, the polyhydric lower alcohol and the monohydric lower alcohol in the case where the cosmetic composition of the present invention is an oil-in-water emulsion composition.

What is claimed is:

1. A cosmetic composition comprising an associative thickener, which is composed of a compound shown in Formula (1),

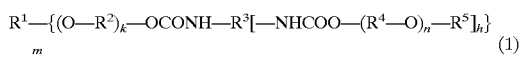

$$R^1—\{(O—R^2)_k—OCONH—R^3[—NHCOO—(R^4—O)_n—R^5]_h\}_m \quad (1)$$

wherein $R^1$, $R^2$ and $R^4$ each is a hydrocarbon group, which may be the same or different each other, $R^3$ is a hydrocarbon group, which may have urethane bond; $R^5$ is a straight chain hydrocarbon group, m is an integer of 2 or more; h is an integer of 1 or more; and k and n each is an integer within the range of 0 to 1000, respectively.

2. The cosmetic composition according to claim 1, wherein the associative thickener is an alkylene group having 2–4 carbon atoms that $R^2$ and/or $R^4$ each may be the same or different or phenylethylene group.

3. The cosmetic composition according to claim 1, wherein $R^3$ is a residue of polyisocyanate which is shown as $R^3—(NCO)_{h+1}$.

4. The cosmetic composition according to claim 1, wherein the polyisocyanate which is shown as $R^3—(NCO)_{h+1}$ is a polyisocyanate having urethane bond, which is obtained by reacting divalent to octavalent polyol with divalent to tetravalent polyisocyanate.

5. The cosmetic composition according to claim 1, wherein $R^1$ is a residue of polyol which is shown as $R^1—(OH)_m$.

6. The cosmetic composition according to claim 1, wherein $R^5$ is a straight chain having 8–36 carbon atoms.

7. The cosmetic composition according to claim 1, wherein the associative thickener is a resultant of one or more of polyetherpolyol that is shown as $R^1—[O—R^2)_k—OH]_m$, one or more of polyisocyanate that $R^3$ is shown as $R^3—(NCO)_{h+1}$, and one or more of polyether monoalcohol shown as $HO—(R^4—O)_n—R^5$.

8. The cosmetic composition according to claim 1, wherein said composition comprises 0.01 to 10 wt % of the associative thickener.

9. The cosmetic composition according to claim 1, wherein said composition further comprises a water-soluble polymer.

10. The cosmetic composition according to claim 9, wherein viscosity ratio of water-soluble polymer/associative thickener is 0.01 to 100.

11. The cosmetic composition according to claim 1, wherein said composition further comprises a polyhydric lower alcohol.

12. The cosmetic composition according to claim 11, wherein said composition comprises 0.01 to 10 wt % of the associative thickener and 0.1 to 30 wt % of the polyhydric lower alcohol.

13. The cosmetic composition according to claim 1, wherein said composition further comprises a monohydric lower alcohol.

14. The cosmetic composition according to claim 13, wherein said composition comprises 0.01 to 10 wt % of the associative thickener and 0.1 to 30 wt % of the monohydric lower alcohol.

15. The cosmetic composition according to claim 9, wherein said cosmetic composition is an oil-in-water emulsion composition.

16. The cosmetic composition according to claim 15, wherein said composition comprises 0.1 to 5 wt % of the associative thickener, 40 wt % or less of an oily ingredient, and ten times or less of cmc (critical micellar concentration) of an ionic surfactant.

17. The cosmetic composition according to claim 15, wherein said composition comprises 0.1 to 5 wt % of the associative thickener, 40 wt % or less of the oily ingredient, and 10 wt % or less of a nonionic surfactant whose HLB is 12 or less.

18. The cosmetic composition according to claim 15, wherein said composition comprises 0.1 to 5 wt % of the associative thickener, 40 wt % or less of the oily ingredient, and 8 wt % or less of the nonionic surfactant whose HLB is 15 or less.

19. The cosmetic composition according to claim 15, wherein said composition comprises 0.1 to 5 wt % of the associative thickener, 40 wt % or less of the oily ingredient, and 6 wt % or less of the nonionic surfactant whose HLB is 15 or more.

* * * * *

UNITED STATES PATENT AND TRADEMARK OFFICE
CERTIFICATE OF CORRECTION

PATENT NO.     : 6,440,431 B1
DATED          : August 27, 2002
INVENTOR(S)    : Katsunori Yoshida, Toshio Yanaki and Isamu Kaneda It is certified that error appears in the above-identified patent and that said Letters Patent is hereby corrected as shown below:

<u>Column 33,</u>
Line 61, after "different" insert -- from --.

<u>Column 34,</u>
Lines 18-19, delete "$R^1\text{-}[O\text{-}R^2]_k\text{-}OH]_m$" and substitute therefore -- $R^1\text{-}[(O\text{-}R^2)_k\text{-}OH]_m$ --.

Signed and Sealed this

First Day of April, 2003

JAMES E. ROGAN
*Director of the United States Patent and Trademark Office*